United States Patent
Tochterman et al.

(10) Patent No.: US 7,867,547 B2
(45) Date of Patent: Jan. 11, 2011

(54) SELECTIVELY COATING LUMINAL SURFACES OF STENTS

(75) Inventors: Andrew J. Tochterman, Palo Alto, CA (US); William J. Fox, San Carlos, CA (US); Nathan Harold, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1361 days.

(21) Appl. No.: 11/312,139

(22) Filed: Dec. 19, 2005

(65) Prior Publication Data
US 2007/0141232 A1    Jun. 21, 2007

(51) Int. Cl.
*B05D 3/02* (2006.01)
*B05D 1/02* (2006.01)
*B05D 1/32* (2006.01)
*B05C 13/00* (2006.01)

(52) U.S. Cl. .............. 427/2.1; 427/2.24; 427/2.25; 427/236; 427/282; 427/300; 427/372.2; 118/502; 118/504

(58) Field of Classification Search ......... 427/230, 427/256, 282, 300, 2.1–2.31, 236, 372.2; 118/502, 504
See application file for complete search history.

(56) References Cited

U.S. PATENT DOCUMENTS

| | | | |
|---|---|---|---|
| 2,072,303 A | 3/1937 | Herrmann et al. | |
| 2,386,454 A | 10/1945 | Frosch et al. | |
| 2,647,017 A | 7/1953 | Coulliette | |
| 2,701,559 A | 2/1955 | Cooper | |
| 2,845,346 A | 7/1958 | Scanlon et al. | |
| 3,016,875 A | 1/1962 | Ballentine, Jr. et al. | |
| 3,288,728 A | 11/1966 | Gorham | |
| 3,687,135 A | 8/1972 | Stroganov et al. | |
| 3,773,737 A | 11/1973 | Goodman et al. | |
| 3,827,139 A | 8/1974 | Norteman | |
| 3,839,743 A | 10/1974 | Schwarcz | |
| 3,849,514 A | 11/1974 | Gray, Jr. et al. | |
| 3,882,816 A | 5/1975 | Rooz et al. | |

(Continued)

FOREIGN PATENT DOCUMENTS

CA    2 008 312    7/1990

(Continued)

OTHER PUBLICATIONS

U.S. Appl. No. 09/894,293, filed Jun. 27, 2001, Roorda et al.

(Continued)

*Primary Examiner*—Frederick J Parker
*Assistant Examiner*—Cachet I Sellman
(74) *Attorney, Agent, or Firm*—Squire, Sanders & Dempsey L.L.P.

(57) ABSTRACT

With abluminal side of a stent masked, the luminal side of the stent is selectively coated with a substance, such as an anticoagulant, a platelet inhibitor and/or a pro-healing substance. The stent can be masked by inserting it into a rigid mandrel chamber or by compressing a masking sleeve onto the outer side of the stent. A spray nozzle inserted into the masked stent spray coats the substance onto the luminal side. The sprayed coating can be cured onto the stent such as by inserting an electrical-resistance heater bar into the stent.

23 Claims, 6 Drawing Sheets

U.S. PATENT DOCUMENTS

| | | |
|---|---|---|
| 3,900,632 A | 8/1975 | Robinson |
| 3,995,075 A | 11/1976 | Cernauskas et al. |
| 4,011,388 A | 3/1977 | Murphy et al. |
| 4,075,045 A | 2/1978 | Rideout |
| 4,082,212 A | 4/1978 | Headrick et al. |
| 4,104,410 A | 8/1978 | Malecki |
| 4,110,497 A | 8/1978 | Hoel |
| 4,132,357 A | 1/1979 | Blackinton |
| 4,164,524 A | 8/1979 | Ward et al. |
| 4,201,149 A | 5/1980 | Koester et al. |
| 4,226,243 A | 10/1980 | Shalaby et al. |
| 4,269,713 A | 5/1981 | Yamashita et al. |
| 4,321,711 A | 3/1982 | Mano |
| 4,323,071 A | 4/1982 | Simpson et al. |
| 4,329,383 A | 5/1982 | Joh |
| 4,338,942 A | 7/1982 | Fogarty |
| 4,343,931 A | 8/1982 | Barrows |
| 4,346,028 A | 8/1982 | Griffith |
| 4,439,185 A | 3/1984 | Lundquist |
| 4,459,252 A | 7/1984 | MacGregor |
| 4,489,670 A | 12/1984 | Mosser et al. |
| 4,516,972 A | 5/1985 | Samson et al. |
| 4,529,792 A | 7/1985 | Barrows |
| 4,538,622 A | 9/1985 | Samson et al. |
| 4,554,929 A | 11/1985 | Samson et al. |
| 4,560,374 A | 12/1985 | Hammerslag |
| 4,573,470 A | 3/1986 | Samson |
| 4,596,574 A | 6/1986 | Urist |
| 4,599,085 A | 7/1986 | Riess et al. |
| 4,608,984 A | 9/1986 | Fogarty |
| 4,611,051 A | 9/1986 | Hayes et al. |
| 4,612,009 A | 9/1986 | Drobnik et al. |
| 4,616,593 A | 10/1986 | Kawamura et al. |
| 4,616,652 A | 10/1986 | Simpson |
| 4,629,563 A | 12/1986 | Wrasidlo |
| 4,633,873 A | 1/1987 | Dumican et al. |
| 4,638,805 A | 1/1987 | Powell |
| 4,640,846 A | 2/1987 | Kuo |
| 4,656,083 A | 4/1987 | Hoffman et al. |
| 4,656,242 A | 4/1987 | Swan et al. |
| 4,699,611 A | 10/1987 | Bowden |
| 4,702,252 A | 10/1987 | Brooks |
| 4,718,907 A | 1/1988 | Karwoski et al. |
| 4,722,335 A | 2/1988 | Vilasi |
| 4,723,549 A | 2/1988 | Wholey et al. |
| 4,732,152 A | 3/1988 | Wallstén et al. |
| 4,733,665 A | 3/1988 | Palmaz |
| 4,739,762 A | 4/1988 | Palmaz |
| 4,740,207 A | 4/1988 | Kreamer |
| 4,743,252 A | 5/1988 | Martin, Jr. et al. |
| 4,748,982 A | 6/1988 | Horzewski et al. |
| 4,762,128 A | 8/1988 | Rosenbluth |
| 4,768,507 A | 9/1988 | Fischell et al. |
| 4,774,039 A | 9/1988 | Wrasidlo |
| 4,776,337 A | 10/1988 | Palmaz |
| 4,798,585 A | 1/1989 | Inoue et al. |
| 4,800,882 A | 1/1989 | Gianturco |
| 4,816,339 A | 3/1989 | Tu et al. |
| 4,818,559 A | 4/1989 | Hama et al. |
| 4,822,535 A | 4/1989 | Ekman et al. |
| 4,828,561 A | 5/1989 | Woodroof |
| 4,839,055 A | 6/1989 | Ishizaki et al. |
| 4,846,791 A | 7/1989 | Hattler et al. |
| 4,850,999 A | 7/1989 | Planck |
| 4,865,870 A | 9/1989 | Hu et al. |
| 4,865,879 A | 9/1989 | Finlay |
| 4,871,542 A | 10/1989 | Vilhardt |
| 4,877,030 A | 10/1989 | Beck et al. |
| 4,878,906 A | 11/1989 | Lindemann et al. |
| 4,879,135 A | 11/1989 | Greco et al. |
| 4,880,683 A | 11/1989 | Stow |
| 4,882,168 A | 11/1989 | Casey et al. |
| 4,886,062 A | 12/1989 | Wiktor |
| 4,893,623 A | 1/1990 | Rosenbluth |
| 4,902,289 A | 2/1990 | Yannas |
| 4,906,423 A | 3/1990 | Frisch |
| 4,931,287 A | 6/1990 | Bae et al. |
| 4,932,353 A | 6/1990 | Kawata et al. |
| 4,941,870 A | 7/1990 | Okada et al. |
| 4,943,346 A | 7/1990 | Mattelin |
| 4,950,227 A | 8/1990 | Savin et al. |
| 4,955,899 A | 9/1990 | Della Corna et al. |
| 4,967,606 A | 11/1990 | Wells et al. |
| 4,976,736 A | 12/1990 | White et al. |
| 4,977,901 A | 12/1990 | Ofstead |
| 4,988,356 A | 1/1991 | Crittenden et al. |
| 4,992,312 A | 2/1991 | Frisch |
| 4,994,033 A | 2/1991 | Shockey et al. |
| 4,994,298 A | 2/1991 | Yasuda |
| 4,994,560 A | 2/1991 | Kruper, Jr. et al. |
| 5,015,505 A | 5/1991 | Cetnar |
| 5,017,420 A | 5/1991 | Marikar |
| 5,019,090 A | 5/1991 | Pinchuk |
| 5,019,096 A | 5/1991 | Fox, Jr. et al. |
| 5,028,597 A | 7/1991 | Kodama et al. |
| 5,033,405 A | 7/1991 | Yamada et al. |
| 5,037,392 A | 8/1991 | Hillstead |
| 5,037,427 A | 8/1991 | Harada et al. |
| 5,040,548 A | 8/1991 | Yock |
| 5,047,050 A | 9/1991 | Arpesani |
| 5,049,132 A | 9/1991 | Shaffer et al. |
| 5,053,048 A | 10/1991 | Pinchuk |
| 5,059,166 A | 10/1991 | Fischell |
| 5,059,169 A | 10/1991 | Zilber |
| 5,059,211 A | 10/1991 | Stack et al. |
| 5,062,829 A | 11/1991 | Pryor et al. |
| 5,064,435 A | 11/1991 | Porter |
| 5,078,720 A | 1/1992 | Burton et al. |
| 5,081,394 A | 1/1992 | Morishita et al. |
| 5,084,065 A | 1/1992 | Weldon et al. |
| 5,085,629 A | 2/1992 | Goldberg et al. |
| 5,087,244 A | 2/1992 | Wolinsky et al. |
| 5,087,394 A | 2/1992 | Keith |
| 5,095,848 A | 3/1992 | Ikeno |
| 5,100,429 A | 3/1992 | Sinofsky et al. |
| 5,100,992 A | 3/1992 | Cohn et al. |
| 5,102,402 A | 4/1992 | Dror et al. |
| 5,104,410 A | 4/1992 | Chowdhary |
| 5,108,416 A | 4/1992 | Ryan et al. |
| 5,108,417 A | 4/1992 | Sawyer |
| 5,108,755 A | 4/1992 | Daniels et al. |
| 5,112,457 A | 5/1992 | Marchant |
| 5,116,318 A | 5/1992 | Hillstead |
| 5,116,365 A | 5/1992 | Hillstead |
| 5,123,917 A | 6/1992 | Lee |
| 5,127,362 A | 7/1992 | Iwatsu et al. |
| 5,133,742 A | 7/1992 | Pinchuk |
| 5,134,192 A | 7/1992 | Feijen et al. |
| 5,147,370 A | 9/1992 | McNamara et al. |
| 5,156,623 A | 10/1992 | Hakamatsuka et al. |
| 5,156,911 A | 10/1992 | Stewart |
| 5,158,548 A | 10/1992 | Lau et al. |
| 5,163,951 A | 11/1992 | Pinchuk et al. |
| 5,163,952 A | 11/1992 | Froix |
| 5,163,958 A | 11/1992 | Pinchuk |
| 5,165,919 A | 11/1992 | Sasaki et al. |
| 5,167,614 A | 12/1992 | Tessmann et al. |
| 5,171,445 A | 12/1992 | Zepf |
| 5,176,638 A | 1/1993 | Don Michael |
| 5,188,734 A | 2/1993 | Zepf |
| 5,192,311 A | 3/1993 | King et al. |
| 5,197,977 A | 3/1993 | Hoffman, Jr. et al. |
| 5,201,314 A | 4/1993 | Bosley et al. |
| 5,205,822 A | 4/1993 | Johnson et al. |

| | | | | | |
|---|---|---|---|---|---|
| 5,213,561 A | 5/1993 | Weinstein et al. | 5,415,938 A | 5/1995 | Cahalan et al. |
| 5,213,576 A | 5/1993 | Abiuso et al. | 5,417,981 A | 5/1995 | Endo et al. |
| 5,219,980 A | 6/1993 | Swidler | 5,421,955 A | 6/1995 | Lau et al. |
| 5,222,971 A | 6/1993 | Willard et al. | 5,423,849 A | 6/1995 | Engelson et al. |
| 5,225,750 A | 7/1993 | Higuchi et al. | 5,423,885 A | 6/1995 | Williams |
| 5,226,889 A | 7/1993 | Sheiban | 5,429,618 A | 7/1995 | Keogh |
| 5,226,913 A | 7/1993 | Pinchuk | 5,441,515 A | 8/1995 | Khosravi et al. |
| 5,229,045 A | 7/1993 | Soldani | 5,443,458 A | 8/1995 | Eury et al. |
| 5,229,172 A | 7/1993 | Cahalan et al. | 5,443,496 A | 8/1995 | Schwartz et al. |
| 5,232,444 A | 8/1993 | Just et al. | 5,443,500 A | 8/1995 | Sigwart |
| 5,234,456 A | 8/1993 | Silvestrini | 5,445,646 A | 8/1995 | Euteneuer et al. |
| 5,234,457 A | 8/1993 | Andersen | 5,447,724 A | 9/1995 | Helmus et al. |
| 5,236,447 A | 8/1993 | Kubo et al. | 5,451,233 A | 9/1995 | Yock |
| 5,242,399 A | 9/1993 | Lau et al. | 5,455,040 A | 10/1995 | Marchant |
| 5,254,089 A | 10/1993 | Wang | 5,456,661 A | 10/1995 | Narciso, Jr. |
| 5,254,091 A | 10/1993 | Aliahmad et al. | 5,456,713 A | 10/1995 | Chuter |
| 5,258,020 A | 11/1993 | Froix | 5,458,615 A | 10/1995 | Klemm et al. |
| 5,258,419 A | 11/1993 | Rolando et al. | 5,458,683 A | 10/1995 | Taylor et al. |
| 5,264,246 A | 11/1993 | Ikeno | 5,460,610 A | 10/1995 | Don Michael |
| 5,269,802 A | 12/1993 | Garber | 5,462,990 A | 10/1995 | Hubbell et al. |
| 5,272,012 A | 12/1993 | Opolski | 5,464,450 A | 11/1995 | Buscemi et al. |
| 5,278,200 A | 1/1994 | Coury et al. | 5,464,650 A | 11/1995 | Berg et al. |
| 5,279,594 A | 1/1994 | Jackson | 5,470,313 A | 11/1995 | Crocker et al. |
| 5,282,823 A | 2/1994 | Schwartz et al. | 5,470,603 A | 11/1995 | Staniforth et al. |
| 5,282,860 A | 2/1994 | Matsuno et al. | 5,476,476 A | 12/1995 | Hillstead |
| 5,286,254 A | 2/1994 | Shapland et al. | 5,476,509 A | 12/1995 | Keogh et al. |
| 5,289,831 A | 3/1994 | Bosley | 5,485,496 A | 1/1996 | Lee et al. |
| 5,290,271 A | 3/1994 | Jernberg | 5,496,346 A | 3/1996 | Horzewski et al. |
| 5,292,516 A | 3/1994 | Viegas et al. | 5,500,013 A | 3/1996 | Buscemi et al. |
| 5,298,260 A | 3/1994 | Viegas et al. | 5,501,227 A | 3/1996 | Yock |
| 5,300,295 A | 4/1994 | Viegas et al. | 5,502,158 A | 3/1996 | Sinclair et al. |
| 5,304,200 A | 4/1994 | Spaulding | 5,507,768 A | 4/1996 | Lau et al. |
| 5,306,250 A | 4/1994 | March et al. | 5,511,726 A | 4/1996 | Greenspan et al. |
| 5,306,286 A | 4/1994 | Stack et al. | 5,514,154 A | 5/1996 | Lau et al. |
| 5,306,294 A | 4/1994 | Winston et al. | 5,514,379 A | 5/1996 | Weissleder et al. |
| 5,306,501 A | 4/1994 | Viegas et al. | 5,516,560 A | 5/1996 | Harayama et al. |
| 5,306,786 A | 4/1994 | Moens et al. | 5,516,881 A | 5/1996 | Lee et al. |
| 5,308,338 A | 5/1994 | Helfrich | 5,527,337 A | 6/1996 | Stack et al. |
| 5,308,641 A | 5/1994 | Cahalan et al. | 5,537,729 A | 7/1996 | Kolobow |
| 5,314,472 A | 5/1994 | Fontaine | 5,538,493 A | 7/1996 | Gerken et al. |
| 5,318,531 A | 6/1994 | Leone | 5,545,209 A | 8/1996 | Roberts et al. |
| 5,328,471 A | 7/1994 | Slepian | 5,545,408 A | 8/1996 | Trigg et al. |
| 5,330,500 A | 7/1994 | Song | 5,551,954 A | 9/1996 | Buscemi et al. |
| 5,330,768 A | 7/1994 | Park et al. | 5,554,120 A | 9/1996 | Chen et al. |
| 5,336,518 A | 8/1994 | Narayanan et al. | 5,554,182 A | 9/1996 | Dinh et al. |
| 5,342,283 A | 8/1994 | Good | 5,556,413 A | 9/1996 | Lam |
| 5,342,348 A | 8/1994 | Kaplan | 5,558,642 A | 9/1996 | Schweich, Jr. et al. |
| 5,342,395 A | 8/1994 | Jarrett et al. | 5,558,900 A | 9/1996 | Fan et al. |
| 5,342,621 A | 8/1994 | Eury | 5,562,728 A | 10/1996 | Lazarus et al. |
| 5,344,426 A | 9/1994 | Lau et al. | 5,569,295 A | 10/1996 | Lam |
| 5,344,455 A | 9/1994 | Keogh et al. | 5,569,463 A | 10/1996 | Helmus et al. |
| 5,350,800 A | 9/1994 | Verhoeven et al. | 5,571,135 A | 11/1996 | Fraser et al. |
| 5,356,433 A | 10/1994 | Rowland et al. | 5,571,166 A | 11/1996 | Dinh et al. |
| 5,358,740 A | 10/1994 | Bornside et al. | 5,571,567 A | 11/1996 | Shah |
| 5,360,401 A | 11/1994 | Turnland et al. | 5,578,046 A | 11/1996 | Liu et al. |
| 5,360,443 A | 11/1994 | Barone et al. | 5,578,048 A | 11/1996 | Pasqualucci et al. |
| 5,364,354 A | 11/1994 | Walker et al. | 5,578,073 A | 11/1996 | Haimovich et al. |
| 5,366,504 A | 11/1994 | Andersen et al. | 5,584,877 A | 12/1996 | Miyake et al. |
| 5,368,560 A | 11/1994 | Rambo et al. | 5,588,962 A | 12/1996 | Nicholas et al. |
| 5,370,684 A | 12/1994 | Vallana et al. | 5,591,199 A | 1/1997 | Porter et al. |
| 5,378,511 A | 1/1995 | Cardinali et al. | 5,591,224 A | 1/1997 | Schwartz et al. |
| 5,380,299 A | 1/1995 | Fearnot et al. | 5,591,227 A | 1/1997 | Dinh et al. |
| 5,383,925 A | 1/1995 | Schmitt | 5,591,607 A | 1/1997 | Gryaznov et al. |
| 5,383,927 A | 1/1995 | DeGoicoechea et al. | 5,593,403 A | 1/1997 | Buscemi |
| 5,385,580 A | 1/1995 | Schmitt | 5,593,434 A | 1/1997 | Williams |
| 5,387,450 A | 2/1995 | Stewart | 5,595,722 A | 1/1997 | Grainger et al. |
| 5,389,106 A | 2/1995 | Tower | 5,599,301 A | 2/1997 | Jacobs et al. |
| 5,399,666 A | 3/1995 | Ford | 5,599,307 A | 2/1997 | Bacher et al. |
| 5,405,472 A | 4/1995 | Leone | 5,599,352 A | 2/1997 | Dinh et al. |
| 5,409,495 A | 4/1995 | Osborn | 5,599,922 A | 2/1997 | Gryaznov et al. |
| 5,411,466 A | 5/1995 | Hess | 5,603,721 A | 2/1997 | Lau et al. |
| 5,411,477 A | 5/1995 | Saab | 5,605,696 A | 2/1997 | Eury et al. |
| 5,412,035 A | 5/1995 | Schmitt et al. | 5,607,442 A | 3/1997 | Fischell et al. |

| Patent No. | Date | Inventor(s) |
|---|---|---|
| 5,607,467 A | 3/1997 | Froix |
| 5,609,629 A | 3/1997 | Fearnot et al. |
| 5,610,241 A | 3/1997 | Lee et al. |
| 5,611,775 A | 3/1997 | Machold et al. |
| 5,616,338 A | 4/1997 | Fox, Jr. et al. |
| 5,618,298 A | 4/1997 | Simon |
| 5,618,299 A | 4/1997 | Khosravi et al. |
| 5,620,420 A | 4/1997 | Kriesel |
| 5,624,411 A | 4/1997 | Tuch |
| 5,628,730 A | 5/1997 | Shapland et al. |
| 5,628,755 A | 5/1997 | Heller et al. |
| 5,628,781 A | 5/1997 | Williams et al. |
| 5,628,785 A | 5/1997 | Schwartz et al. |
| 5,628,786 A | 5/1997 | Banas et al. |
| 5,629,077 A | 5/1997 | Turnlund et al. |
| 5,631,135 A | 5/1997 | Gryaznov et al. |
| 5,632,771 A | 5/1997 | Boatman et al. |
| 5,632,840 A | 5/1997 | Campbell |
| 5,637,113 A | 6/1997 | Tartaglia et al. |
| 5,643,580 A | 7/1997 | Subramaniam |
| 5,644,020 A | 7/1997 | Timmermann et al. |
| 5,645,559 A | 7/1997 | Hachtman et al. |
| 5,649,951 A | 7/1997 | Davidson |
| 5,649,977 A | 7/1997 | Campbell |
| 5,653,691 A | 8/1997 | Rupp et al. |
| 5,656,080 A | 8/1997 | Staniforth et al. |
| 5,656,082 A | 8/1997 | Takatsuki et al. |
| 5,658,995 A | 8/1997 | Kohn et al. |
| 5,667,523 A | 9/1997 | Bynon et al. |
| 5,667,767 A | 9/1997 | Greff et al. |
| 5,667,796 A | 9/1997 | Otten |
| 5,670,558 A | 9/1997 | Onishi et al. |
| 5,674,242 A | 10/1997 | Phan et al. |
| 5,679,400 A | 10/1997 | Tuch |
| 5,687,906 A | 11/1997 | Nakagawa |
| 5,693,085 A | 12/1997 | Buirge et al. |
| 5,693,376 A | 12/1997 | Fetherston et al. |
| 5,695,498 A | 12/1997 | Tower |
| 5,695,810 A | 12/1997 | Dubin et al. |
| 5,697,967 A | 12/1997 | Dinh et al. |
| 5,700,286 A | 12/1997 | Tartaglia et al. |
| 5,702,754 A | 12/1997 | Zhong |
| 5,702,818 A | 12/1997 | Cahalan et al. |
| 5,707,385 A | 1/1998 | Williams |
| 5,711,763 A | 1/1998 | Nonami et al. |
| 5,711,812 A | 1/1998 | Chapek et al. |
| 5,711,958 A | 1/1998 | Cohn et al. |
| 5,713,949 A | 2/1998 | Jayaraman |
| 5,716,981 A | 2/1998 | Hunter et al. |
| 5,718,726 A | 2/1998 | Amon et al. |
| 5,720,726 A | 2/1998 | Marcadis et al. |
| 5,721,131 A | 2/1998 | Rudolph et al. |
| 5,722,984 A | 3/1998 | Fischell et al. |
| 5,723,219 A | 3/1998 | Kolluri et al. |
| 5,725,549 A | 3/1998 | Lam |
| 5,726,297 A | 3/1998 | Gryaznov et al. |
| 5,728,068 A | 3/1998 | Leone et al. |
| 5,728,751 A | 3/1998 | Patnaik |
| 5,730,698 A | 3/1998 | Fischell et al. |
| 5,733,326 A | 3/1998 | Tomonto et al. |
| 5,733,327 A | 3/1998 | Igaki et al. |
| 5,733,330 A | 3/1998 | Cox |
| 5,733,564 A | 3/1998 | Lehtinen |
| 5,733,925 A | 3/1998 | Kunz et al. |
| 5,735,897 A | 4/1998 | Buirge |
| 5,741,554 A | 4/1998 | Tisone |
| 5,741,881 A | 4/1998 | Patnaik |
| 5,746,745 A | 5/1998 | Abele et al. |
| 5,746,998 A | 5/1998 | Torchilin et al. |
| 5,756,457 A | 5/1998 | Wang et al. |
| 5,756,476 A | 5/1998 | Epstein et al. |
| 5,756,553 A | 5/1998 | Iguchi et al. |
| 5,759,205 A | 6/1998 | Valentini |
| 5,759,474 A | 6/1998 | Rupp et al. |
| 5,765,682 A | 6/1998 | Bley et al. |
| 5,766,204 A | 6/1998 | Porter et al. |
| 5,766,239 A | 6/1998 | Cox |
| 5,766,710 A | 6/1998 | Turnlund et al. |
| 5,769,883 A | 6/1998 | Buscemi et al. |
| 5,769,884 A | 6/1998 | Solovay |
| 5,770,609 A | 6/1998 | Grainger et al. |
| 5,772,864 A | 6/1998 | Møller et al. |
| 5,776,184 A | 7/1998 | Tuch |
| 5,780,807 A | 7/1998 | Saunders |
| 5,782,742 A | 7/1998 | Crocker et al. |
| 5,783,657 A | 7/1998 | Pavlin et al. |
| 5,788,626 A | 8/1998 | Thompson |
| 5,788,979 A | 8/1998 | Alt et al. |
| 5,800,392 A | 9/1998 | Racchini |
| 5,800,516 A | 9/1998 | Fine et al. |
| 5,804,318 A | 9/1998 | Pinchuk et al. |
| 5,807,244 A | 9/1998 | Barot |
| 5,810,871 A | 9/1998 | Tuckey et al. |
| 5,810,873 A | 9/1998 | Morales |
| 5,811,151 A | 9/1998 | Hendriks et al. |
| 5,811,447 A | 9/1998 | Kunz et al. |
| 5,820,917 A | 10/1998 | Tuch |
| 5,823,996 A | 10/1998 | Sparks |
| 5,824,048 A | 10/1998 | Tuch |
| 5,824,049 A | 10/1998 | Ragheb et al. |
| 5,824,056 A | 10/1998 | Rosenberg |
| 5,826,586 A | 10/1998 | Mishra et al. |
| 5,830,178 A | 11/1998 | Jones et al. |
| 5,830,179 A | 11/1998 | Mikus et al. |
| 5,830,217 A | 11/1998 | Ryan |
| 5,830,461 A | 11/1998 | Billiar |
| 5,830,879 A | 11/1998 | Isner |
| 5,833,644 A | 11/1998 | Zadno-Azizi et al. |
| 5,833,651 A | 11/1998 | Donovan et al. |
| 5,833,659 A | 11/1998 | Kranys |
| 5,834,582 A | 11/1998 | Sinclair et al. |
| 5,836,962 A | 11/1998 | Gianotti |
| 5,836,965 A | 11/1998 | Jendersee et al. |
| 5,837,008 A | 11/1998 | Berg et al. |
| 5,837,313 A | 11/1998 | Ding et al. |
| 5,837,835 A | 11/1998 | Gryaznov et al. |
| 5,840,009 A | 11/1998 | Fischell et al. |
| 5,840,083 A | 11/1998 | Braach-Maksvytis |
| 5,843,033 A | 12/1998 | Ropiak |
| 5,843,119 A | 12/1998 | Schulewitz |
| 5,843,172 A | 12/1998 | Yan |
| 5,846,247 A | 12/1998 | Unsworth et al. |
| 5,849,859 A | 12/1998 | Acemoglu |
| 5,851,508 A | 12/1998 | Greff et al. |
| 5,853,408 A | 12/1998 | Muni |
| 5,854,207 A | 12/1998 | Lee et al. |
| 5,854,376 A | 12/1998 | Higashi |
| 5,855,598 A | 1/1999 | Pinchuk |
| 5,855,600 A | 1/1999 | Alt |
| 5,855,612 A | 1/1999 | Ohthuki et al. |
| 5,855,618 A | 1/1999 | Patnaik et al. |
| 5,855,684 A | 1/1999 | Bergmann |
| 5,857,998 A | 1/1999 | Barry |
| 5,858,556 A | 1/1999 | Eckhart et al. |
| 5,858,746 A | 1/1999 | Hubbell et al. |
| 5,858,990 A | 1/1999 | Walsh |
| 5,860,954 A | 1/1999 | Ropiak |
| 5,865,814 A | 2/1999 | Tuch |
| 5,866,113 A | 2/1999 | Hendriks et al. |
| 5,868,781 A | 2/1999 | Killion |
| 5,869,127 A | 2/1999 | Zhong |
| 5,871,436 A | 2/1999 | Eury |
| 5,871,437 A | 2/1999 | Alt |
| 5,873,904 A | 2/1999 | Ragheb et al. |
| 5,874,101 A | 2/1999 | Zhong et al. |
| 5,874,109 A | 2/1999 | Ducheyne et al. |

| | | | | | | |
|---|---|---|---|---|---|---|
| 5,874,165 A | 2/1999 | Drumheller | | 6,019,789 A | 2/2000 | Dinh et al. |
| 5,874,355 A | 2/1999 | Huang et al. | | 6,024,918 A | 2/2000 | Hendriks et al. |
| 5,876,426 A | 3/1999 | Kume et al. | | 6,027,510 A | 2/2000 | Alt |
| 5,876,433 A | 3/1999 | Lunn | | 6,027,526 A | 2/2000 | Limon et al. |
| 5,876,743 A | 3/1999 | Ibsen et al. | | 6,030,371 A | 2/2000 | Pursley |
| 5,877,224 A | 3/1999 | Brocchini et al. | | 6,033,582 A | 3/2000 | Lee et al. |
| 5,877,263 A | 3/1999 | Patnaik et al. | | 6,033,719 A | 3/2000 | Keogh |
| 5,879,713 A | 3/1999 | Roth et al. | | 6,034,204 A | 3/2000 | Mohr et al. |
| 5,883,011 A | 3/1999 | Lin et al. | | 6,042,606 A | 3/2000 | Frantzen |
| 5,888,533 A | 3/1999 | Dunn | | 6,042,875 A | 3/2000 | Ding et al. |
| 5,891,108 A | 4/1999 | Leone et al. | | 6,045,899 A | 4/2000 | Wang et al. |
| 5,891,192 A | 4/1999 | Murayama et al. | | 6,048,964 A | 4/2000 | Lee et al. |
| 5,891,507 A | 4/1999 | Jayaraman | | 6,051,021 A | 4/2000 | Frid |
| 5,893,840 A | 4/1999 | Hull et al. | | 6,051,576 A | 4/2000 | Ashton et al. |
| 5,893,852 A | 4/1999 | Morales | | 6,051,648 A | 4/2000 | Rhee et al. |
| 5,895,407 A | 4/1999 | Jayaraman | | 6,054,553 A | 4/2000 | Groth et al. |
| 5,897,911 A | 4/1999 | Loeffler | | 6,056,906 A | 5/2000 | Werneth et al. |
| 5,897,955 A | 4/1999 | Drumheller | | 6,056,993 A | 5/2000 | Leidner et al. |
| 5,898,178 A | 4/1999 | Bunker | | 6,059,714 A | 5/2000 | Armini et al. |
| 5,902,631 A | 5/1999 | Wang et al. | | 6,059,752 A | 5/2000 | Segal |
| 5,902,875 A | 5/1999 | Roby et al. | | 6,059,810 A | 5/2000 | Brown et al. |
| 5,905,168 A | 5/1999 | Dos Santos et al. | | 6,060,451 A | 5/2000 | DiMaio et al. |
| 5,906,759 A | 5/1999 | Richter | | 6,060,518 A | 5/2000 | Kabanov et al. |
| 5,910,564 A | 6/1999 | Gruning et al. | | 6,063,092 A | 5/2000 | Shin |
| 5,911,752 A | 6/1999 | Dustrude et al. | | 6,066,156 A | 5/2000 | Yan |
| 5,914,182 A | 6/1999 | Drumheller | | 6,068,202 A | 5/2000 | Hynes et al. |
| 5,914,387 A | 6/1999 | Roby et al. | | 6,071,266 A | 6/2000 | Kelley |
| 5,916,234 A | 6/1999 | Lam | | 6,071,305 A | 6/2000 | Brown et al. |
| 5,916,870 A | 6/1999 | Lee et al. | | 6,074,659 A | 6/2000 | Kunz et al. |
| 5,919,893 A | 7/1999 | Roby et al. | | 6,080,099 A | 6/2000 | Slater et al. |
| 5,921,416 A | 7/1999 | Uchara | | 6,080,177 A | 6/2000 | Igaki et al. |
| 5,922,005 A | 7/1999 | Richter et al. | | 6,080,190 A | 6/2000 | Schwartz |
| 5,922,393 A | 7/1999 | Jayaraman | | 6,080,488 A | 6/2000 | Hostettler et al. |
| 5,925,552 A | 7/1999 | Keogh et al. | | 6,083,258 A | 7/2000 | Yadav |
| 5,925,720 A | 7/1999 | Kataoka et al. | | 6,086,610 A | 7/2000 | Duerig et al. |
| 5,928,279 A | 7/1999 | Shannon et al. | | 6,090,330 A | 7/2000 | Gawa et al. |
| 5,928,916 A | 7/1999 | Keogh | | 6,093,199 A | 7/2000 | Brown et al. |
| 5,932,299 A | 8/1999 | Katoot | | 6,093,463 A | 7/2000 | Thakrar |
| 5,935,135 A | 8/1999 | Bramfitt et al. | | 6,096,070 A | 8/2000 | Ragheb et al. |
| 5,942,209 A | 8/1999 | Leavitt et al. | | 6,096,525 A | 8/2000 | Patnaik |
| 5,947,993 A | 9/1999 | Morales | | 6,099,455 A | 8/2000 | Columbo et al. |
| 5,948,018 A | 9/1999 | Dereume et al. | | 6,099,559 A | 8/2000 | Nolting |
| 5,948,428 A | 9/1999 | Lee et al. | | 6,099,561 A | 8/2000 | Alt |
| 5,951,881 A | 9/1999 | Rogers et al. | | 6,099,562 A | 8/2000 | Ding et al. |
| 5,954,744 A | 9/1999 | Phan et al. | | 6,103,230 A | 8/2000 | Billiar et al. |
| 5,955,509 A | 9/1999 | Webber et al. | | 6,106,454 A | 8/2000 | Berg et al. |
| 5,957,975 A | 9/1999 | Lafont et al. | | 6,106,530 A | 8/2000 | Harada |
| 5,958,385 A | 9/1999 | Tondeur et al. | | 6,106,889 A | 8/2000 | Beavers et al. |
| 5,962,138 A | 10/1999 | Kolluri et al. | | 6,107,416 A | 8/2000 | Patnaik et al. |
| 5,965,720 A | 10/1999 | Gryaznov et al. | | 6,110,180 A | 8/2000 | Foreman et al. |
| 5,968,091 A | 10/1999 | Pinchuk et al. | | 6,110,188 A | 8/2000 | Narciso, Jr. |
| 5,968,092 A | 10/1999 | Buscemi et al. | | 6,110,483 A | 8/2000 | Whitbourne et al. |
| 5,969,422 A | 10/1999 | Ting et al. | | 6,113,629 A | 9/2000 | Ken |
| 5,971,954 A | 10/1999 | Conway et al. | | 6,117,479 A | 9/2000 | Hogan et al. |
| 5,972,027 A | 10/1999 | Johnson | | 6,117,979 A | 9/2000 | Hendriks et al. |
| 5,972,029 A | 10/1999 | Fuisz | | 6,120,477 A | 9/2000 | Campbell et al. |
| 5,972,505 A | 10/1999 | Phillips et al. | | 6,120,491 A | 9/2000 | Kohn et al. |
| 5,976,155 A | 11/1999 | Foreman et al. | | 6,120,535 A | 9/2000 | McDonald et al. |
| 5,976,182 A | 11/1999 | Cox | | 6,120,536 A | 9/2000 | Ding et al. |
| 5,980,564 A | 11/1999 | Stinson | | 6,120,788 A | 9/2000 | Barrows |
| 5,980,928 A | 11/1999 | Terry | | 6,120,847 A | 9/2000 | Yang et al. |
| 5,980,972 A | 11/1999 | Ding | | 6,120,904 A | 9/2000 | Hostettler et al. |
| 5,981,568 A | 11/1999 | Kunz et al. | | 6,121,027 A | 9/2000 | Clapper et al. |
| 5,984,449 A | 11/1999 | Tajika et al. | | 6,123,712 A | 9/2000 | Di Caprio et al. |
| 5,986,169 A | 11/1999 | Gjunter | | 6,125,523 A | 10/2000 | Brown et al. |
| 5,997,468 A | 12/1999 | Wolff et al. | | 6,126,686 A | 10/2000 | Badylak et al. |
| 5,997,517 A | 12/1999 | Whitbourne | | 6,127,173 A | 10/2000 | Eckstein et al. |
| 6,010,445 A | 1/2000 | Armini et al. | | 6,129,755 A | 10/2000 | Mathis et al. |
| 6,010,530 A | 1/2000 | Goicoechea | | 6,129,761 A | 10/2000 | Hubbell |
| 6,010,573 A | 1/2000 | Bowlin | | 6,129,928 A | 10/2000 | Sarangapani et al. |
| 6,011,125 A | 1/2000 | Lohmeijer et al. | | 6,132,809 A | 10/2000 | Hynes et al. |
| 6,013,099 A | 1/2000 | Dinh et al. | | 6,136,333 A | 10/2000 | Cohn et al. |
| 6,015,541 A | 1/2000 | Greff et al. | | 6,140,127 A | 10/2000 | Sprague |

| | | | | | | |
|---|---|---|---|---|---|---|
| 6,140,431 A | 10/2000 | Kinker et al. | | 6,273,878 B1 | 8/2001 | Muni |
| 6,143,354 A | 11/2000 | Koulik et al. | | 6,273,908 B1 | 8/2001 | Ndondo-Lay |
| 6,143,370 A | 11/2000 | Panagiotou et al. | | 6,273,910 B1 | 8/2001 | Limon |
| 6,149,574 A | 11/2000 | Trauthen et al. | | 6,273,913 B1 | 8/2001 | Wright et al. |
| 6,150,630 A | 11/2000 | Perry et al. | | 6,277,110 B1 | 8/2001 | Morales |
| 6,153,252 A | 11/2000 | Hossainy et al. | | 6,277,449 B1 | 8/2001 | Kolluri et al. |
| 6,156,373 A | 12/2000 | Zhong et al. | | 6,279,368 B1 | 8/2001 | Escano et al. |
| 6,159,227 A | 12/2000 | Di Caprio et al. | | 6,281,262 B1 | 8/2001 | Shikinami |
| 6,159,229 A | 12/2000 | Jendersee et al. | | 6,283,947 B1 | 9/2001 | Mirzaee |
| 6,159,951 A | 12/2000 | Karpeisky et al. | | 6,283,949 B1 | 9/2001 | Roorda |
| 6,159,978 A | 12/2000 | Myers et al. | | 6,284,305 B1 | 9/2001 | Ding et al. |
| 6,160,084 A | 12/2000 | Langer et al. | | 6,284,333 B1 | 9/2001 | Wang et al. |
| 6,165,212 A | 12/2000 | Dereume et al. | | 6,287,249 B1 | 9/2001 | Tam et al. |
| 6,165,267 A | 12/2000 | Torczynski | | 6,287,332 B1 | 9/2001 | Bolz et al. |
| 6,166,130 A | 12/2000 | Rhee et al. | | 6,287,628 B1 | 9/2001 | Hossainy et al. |
| 6,168,617 B1 | 1/2001 | Blaeser et al. | | 6,290,721 B1 | 9/2001 | Heath |
| 6,168,619 B1 | 1/2001 | Dinh et al. | | 6,293,966 B1 | 9/2001 | Frantzen |
| 6,169,170 B1 | 1/2001 | Gryaznov et al. | | 6,294,836 B1 | 9/2001 | Paranjpe et al. |
| 6,171,334 B1 | 1/2001 | Cox | | 6,296,603 B1 | 10/2001 | Turnlund et al. |
| 6,171,609 B1 | 1/2001 | Kunz | | 6,299,604 B1 | 10/2001 | Ragheb et al. |
| 6,172,167 B1 | 1/2001 | Stapert et al. | | 6,303,901 B1 | 10/2001 | Perry et al. |
| 6,174,316 B1 | 1/2001 | Tuckey et al. | | 6,306,165 B1 | 10/2001 | Patnaik et al. |
| 6,174,330 B1 | 1/2001 | Stinson | | 6,306,176 B1 | 10/2001 | Whitbourne |
| 6,177,523 B1 | 1/2001 | Reich et al. | | 6,312,459 B1 | 11/2001 | Huang et al. |
| 6,180,632 B1 | 1/2001 | Myers et al. | | 6,319,520 B1 | 11/2001 | Wuthrich et al. |
| 6,183,505 B1 | 2/2001 | Mohn, Jr. et al. | | 6,322,588 B1 | 11/2001 | Ogle et al. |
| 6,187,045 B1 | 2/2001 | Fehring et al. | | 6,322,847 B1 | 11/2001 | Zhong et al. |
| 6,193,727 B1 | 2/2001 | Foreman et al. | | 6,327,772 B1 | 12/2001 | Zadno-Azizi et al. |
| 6,194,034 B1 | 2/2001 | Nishi et al. | | 6,331,191 B1 | 12/2001 | Chobotov |
| 6,197,013 B1 | 3/2001 | Reed et al. | | 6,331,313 B1 | 12/2001 | Wong et al. |
| 6,203,551 B1 | 3/2001 | Wu | | 4,733,665 C2 | 1/2002 | Palmaz |
| 6,203,569 B1 | 3/2001 | Wijay | | 6,335,029 B1 | 1/2002 | Kamath et al. |
| 6,206,915 B1 | 3/2001 | Fagan et al. | | 6,344,035 B1 | 2/2002 | Chudzik et al. |
| 6,209,621 B1 | 4/2001 | Treacy | | 6,346,110 B2 | 2/2002 | Wu |
| 6,210,715 B1 | 4/2001 | Starling et al. | | 6,358,556 B1 | 3/2002 | Ding et al. |
| 6,211,249 B1 | 4/2001 | Cohn et al. | | 6,358,567 B2 | 3/2002 | Pham et al. |
| 6,214,115 B1 | 4/2001 | Taylor et al. | | 6,362,099 B1 | 3/2002 | Gandikota et al. |
| 6,214,407 B1 | 4/2001 | Laube et al. | | 6,364,903 B2 | 4/2002 | Tseng et al. |
| 6,214,901 B1 | 4/2001 | Chudzik et al. | | 6,368,658 B1 | 4/2002 | Schwarz et al. |
| 6,217,586 B1 | 4/2001 | Mackenzie | | 6,372,283 B1 | 4/2002 | Shim et al. |
| 6,217,721 B1 | 4/2001 | Xu et al. | | 6,375,458 B1 | 4/2002 | Moorleghem et al. |
| 6,224,626 B1 | 5/2001 | Steinke | | 6,375,826 B1 | 4/2002 | Wang et al. |
| 6,224,675 B1 | 5/2001 | Prentice et al. | | 6,379,379 B1 | 4/2002 | Wang |
| 6,224,894 B1 | 5/2001 | Jamiolkowski et al. | | 6,379,381 B1 | 4/2002 | Hossainy et al. |
| 6,228,072 B1 | 5/2001 | Omaleki et al. | | 6,383,215 B1 | 5/2002 | Sass |
| 6,228,845 B1 | 5/2001 | Donovan et al. | | 6,387,118 B1 | 5/2002 | Hanson |
| 6,231,590 B1 | 5/2001 | Slaikeu et al. | | 6,387,121 B1 | 5/2002 | Alt |
| 6,231,600 B1 | 5/2001 | Zhong | | 6,387,379 B1 | 5/2002 | Goldberg et al. |
| 6,235,340 B1 | 5/2001 | Lee et al. | | 6,388,043 B1 | 5/2002 | Langer et al. |
| 6,240,616 B1 | 6/2001 | Yan | | 6,395,325 B1 | 5/2002 | Hedge et al. |
| 6,242,041 B1 | 6/2001 | Katoot et al. | | 6,395,326 B1 | 5/2002 | Castro et al. |
| 6,244,575 B1 | 6/2001 | Vaartstra et al. | | 6,406,738 B1 | 6/2002 | Hogan et al. |
| 6,245,076 B1 | 6/2001 | Yan | | 6,409,761 B1 | 6/2002 | Jang |
| 6,245,099 B1 | 6/2001 | Edwin et al. | | 6,413,272 B1 | 7/2002 | Igaki |
| 6,245,103 B1 | 6/2001 | Stinson | | 6,416,543 B1 | 7/2002 | Hilaire et al. |
| 6,245,753 B1 | 6/2001 | Byun et al. | | 6,419,692 B1 | 7/2002 | Yang et al. |
| 6,245,760 B1 | 6/2001 | He et al. | | 6,420,189 B1 | 7/2002 | Lopatin |
| 6,248,129 B1 | 6/2001 | Froix | | 6,423,092 B2 | 7/2002 | Datta et al. |
| 6,248,344 B1 | 6/2001 | Ylanen et al. | | 6,435,798 B1 | 8/2002 | Satoh |
| 6,248,398 B1 | 6/2001 | Talieh et al. | | 6,436,816 B1 | 8/2002 | Lee et al. |
| 6,251,135 B1 | 6/2001 | Stinson et al. | | 6,440,221 B2 | 8/2002 | Shamouilian et al. |
| 6,251,136 B1 | 6/2001 | Guruwaiya et al. | | 6,444,567 B1 | 9/2002 | Besser et al. |
| 6,251,142 B1 | 6/2001 | Bernacca et al. | | 6,447,835 B1 * | 9/2002 | Wang et al. ................. 427/2.24 |
| 6,253,443 B1 | 7/2001 | Johnson | | 6,451,373 B1 | 9/2002 | Hossainy et al. |
| 6,254,632 B1 | 7/2001 | Wu et al. | | 6,454,738 B1 | 9/2002 | Tran et al. |
| 6,258,099 B1 | 7/2001 | Mareiro et al. | | 6,455,424 B1 | 9/2002 | McTeer et al. |
| 6,258,121 B1 | 7/2001 | Yang et al. | | 6,461,632 B1 | 10/2002 | Gogolewski |
| 6,258,371 B1 | 7/2001 | Koulik et al. | | 6,462,284 B1 | 10/2002 | Hashimoto |
| 6,261,320 B1 | 7/2001 | Tam et al. | | 6,464,720 B2 | 10/2002 | Boatman et al. |
| 6,262,034 B1 | 7/2001 | Mathiowitz et al. | | 6,468,906 B1 | 10/2002 | Chan et al. |
| 6,270,504 B1 | 8/2001 | Lorentzen Cornelius et al. | | 6,475,779 B2 | 11/2002 | Mathiowitz et al. |
| 6,270,788 B1 | 8/2001 | Koulik et al. | | 6,479,565 B1 | 11/2002 | Stanley |
| 6,273,850 B1 | 8/2001 | Gambale | | 6,481,262 B2 | 11/2002 | Ching et al. |

| | | |
|---|---|---|
| 6,482,834 B2 | 11/2002 | Spada et al. |
| 6,485,512 B1 | 11/2002 | Cheng |
| 6,488,701 B1 | 12/2002 | Nolting et al. |
| 6,488,773 B1 | 12/2002 | Ehrhardt et al. |
| 6,491,666 B1 | 12/2002 | Santini, Jr. et al. |
| 6,492,615 B1 | 12/2002 | Flanagan |
| 6,494,862 B1 | 12/2002 | Ray et al. |
| 6,494,908 B1 | 12/2002 | Huxel et al. |
| 6,495,156 B2 | 12/2002 | Wenz et al. |
| 6,495,200 B1 | 12/2002 | Chan et al. |
| 6,503,538 B1 | 1/2003 | Chu et al. |
| 6,503,556 B2 | 1/2003 | Harish et al. |
| 6,503,954 B1 | 1/2003 | Bhat et al. |
| 6,504,307 B1 | 1/2003 | Malik et al. |
| 6,506,437 B1 | 1/2003 | Harish et al. |
| 6,510,722 B1 | 1/2003 | Ching et al. |
| 6,511,748 B1 | 1/2003 | Barrows |
| 6,517,534 B1 | 2/2003 | McGovern et al. |
| 6,517,888 B1 | 2/2003 | Weber |
| 6,517,889 B1 | 2/2003 | Jayaraman |
| 6,521,284 B1 | 2/2003 | Parsons et al. |
| 6,524,232 B1 | 2/2003 | Tang et al. |
| 6,524,347 B1 | 2/2003 | Myers et al. |
| 6,527,801 B1 | 3/2003 | Dutta |
| 6,527,863 B1 | 3/2003 | Pacetti et al. |
| 6,528,526 B1 | 3/2003 | Myers et al. |
| 6,530,950 B1 | 3/2003 | Alvarado et al. |
| 6,530,951 B1 | 3/2003 | Bates et al. |
| 6,534,112 B1 | 3/2003 | Bouchier et al. |
| 6,537,589 B1 | 3/2003 | Chae et al. |
| 6,539,607 B1 | 4/2003 | Fehring et al. |
| 6,540,776 B2 | 4/2003 | Sanders Millare et al. |
| 6,540,777 B2 | 4/2003 | Stenzel |
| 6,544,223 B1 | 4/2003 | Kokish |
| 6,544,543 B1 | 4/2003 | Mandrusov et al. |
| 6,544,582 B1 | 4/2003 | Yoe |
| 6,554,758 B2 | 4/2003 | Turnlund et al. |
| 6,554,854 B1 | 4/2003 | Flanagan |
| 6,555,059 B1 | 4/2003 | Myrick et al. |
| 6,555,157 B1 | 4/2003 | Hossainy |
| 6,558,733 B1 | 5/2003 | Hossainy et al. |
| 6,562,136 B1 | 5/2003 | Chappa et al. |
| 6,565,599 B1 | 5/2003 | Hong et al. |
| 6,565,659 B1 | 5/2003 | Pacetti et al. |
| 6,569,191 B1 | 5/2003 | Hogan |
| 6,569,193 B1 | 5/2003 | Cox et al. |
| 6,572,644 B1 | 6/2003 | Moein |
| 6,572,651 B1 | 6/2003 | De Scheerder et al. |
| 6,572,672 B2 | 6/2003 | Yadav et al. |
| 6,574,851 B1 | 6/2003 | Mirizzi |
| 6,575,933 B1 | 6/2003 | Wittenberger et al. |
| 6,582,417 B1 | 6/2003 | Ledesma et al. |
| 6,585,755 B2 | 7/2003 | Jackson et al. |
| 6,585,765 B1 | 7/2003 | Hossainy et al. |
| 6,585,926 B1 | 7/2003 | Mirzaee |
| 6,592,614 B2 | 7/2003 | Lenker et al. |
| 6,592,617 B2 | 7/2003 | Thompson |
| 6,596,296 B1 | 7/2003 | Nelson et al. |
| 6,605,114 B1 | 8/2003 | Yan et al. |
| 6,605,154 B1 | 8/2003 | Villareal |
| 6,605,874 B2 | 8/2003 | Leu et al. |
| 6,610,087 B1 | 8/2003 | Zarbatany et al. |
| 6,613,072 B2 | 9/2003 | Lau et al. |
| 6,613,432 B2 | 9/2003 | Zamora et al. |
| 6,616,765 B1 | 9/2003 | Castro |
| 6,620,617 B2 | 9/2003 | Mathiowitz et al. |
| 6,623,448 B2 | 9/2003 | Slater |
| 6,625,486 B2 | 9/2003 | Lundkvist et al. |
| 6,626,939 B1 | 9/2003 | Burnside et al. |
| 6,635,269 B1 | 10/2003 | Jennissen |
| 6,635,964 B2 | 10/2003 | Maex et al. |
| 6,641,611 B2 | 11/2003 | Jayaraman |
| 6,645,135 B1 | 11/2003 | Bhat |
| 6,645,195 B1 | 11/2003 | Bhat et al. |
| 6,645,243 B1 | 11/2003 | Vallana et al. |
| 6,645,547 B1 | 11/2003 | Shekalim et al. |
| 6,656,162 B2 | 12/2003 | Santini, Jr. et al. |
| 6,656,216 B1 | 12/2003 | Hossainy et al. |
| 6,656,506 B1 | 12/2003 | Wu et al. |
| 6,660,034 B1 | 12/2003 | Mandrusov et al. |
| 6,663,662 B2 | 12/2003 | Pacetti et al. |
| 6,663,880 B1 | 12/2003 | Roorda et al. |
| 6,664,187 B1 | 12/2003 | Ngo et al. |
| 6,664,335 B2 | 12/2003 | Krishnan |
| 6,666,214 B2 | 12/2003 | Canham |
| 6,666,880 B1 | 12/2003 | Chiu et al. |
| 6,667,049 B2 | 12/2003 | Janas et al. |
| 6,669,723 B2 | 12/2003 | Killion et al. |
| 6,669,980 B2 | 12/2003 | Hansen |
| 6,673,154 B1 | 1/2004 | Pacetti et al. |
| 6,673,385 B1 | 1/2004 | Ding et al. |
| 6,676,697 B1 | 1/2004 | Richter |
| 6,676,700 B1 | 1/2004 | Jacobs et al. |
| 6,679,980 B1 | 1/2004 | Andreacchi |
| 6,682,771 B2 | 1/2004 | Zhong et al. |
| 6,689,099 B2 | 2/2004 | Mirzaee |
| 6,689,350 B2 | 2/2004 | Uhrich |
| 6,689,375 B1 | 2/2004 | Wahlig et al. |
| 6,695,920 B1 | 2/2004 | Pacetti et al. |
| 6,699,281 B2 | 3/2004 | Vallana et al. |
| 6,703,307 B2 | 3/2004 | Lopatin et al. |
| 6,706,013 B1 | 3/2004 | Bhat et al. |
| 6,706,273 B1 | 3/2004 | Roessler |
| 6,709,379 B1 | 3/2004 | Brandau et al. |
| 6,709,514 B1 | 3/2004 | Hossainy |
| 6,712,845 B2 | 3/2004 | Hossainy |
| 6,713,119 B2 | 3/2004 | Hossainy et al. |
| 6,716,444 B1 | 4/2004 | Castro et al. |
| 6,719,934 B2 | 4/2004 | Stinson |
| 6,719,989 B1 | 4/2004 | Matsushima et al. |
| 6,720,402 B2 | 4/2004 | Langer et al. |
| 6,723,120 B2 | 4/2004 | Yan |
| 6,723,373 B1 | 4/2004 | Narayanan et al. |
| 6,730,064 B2 | 5/2004 | Ragheb et al. |
| 6,733,768 B2 | 5/2004 | Hossainy et al. |
| 6,740,040 B1 | 5/2004 | Mandrusov et al. |
| 6,743,462 B1 | 6/2004 | Pacetti |
| 6,746,773 B2 | 6/2004 | Llanos et al. |
| 6,749,626 B1 | 6/2004 | Bhat et al. |
| 6,752,826 B2 | 6/2004 | Holloway et al. |
| 6,753,007 B2 | 6/2004 | Haggard et al. |
| 6,753,071 B1 | 6/2004 | Pacetti et al. |
| 6,758,859 B1 | 7/2004 | Dang et al. |
| 6,759,054 B2 | 7/2004 | Chen et al. |
| 6,764,505 B1 | 7/2004 | Hossainy et al. |
| 6,774,278 B1 | 8/2004 | Ragheb et al. |
| 6,776,792 B1 | 8/2004 | Yan et al. |
| 6,776,796 B2 | 8/2004 | Falotico et al. |
| 6,780,424 B2 | 8/2004 | Claude |
| 6,783,793 B1 | 8/2004 | Hossainy et al. |
| 6,790,228 B2 | 9/2004 | Hossainy et al. |
| 6,818,063 B1 | 11/2004 | Kerrigan |
| 6,824,559 B2 | 11/2004 | Michal |
| 6,846,323 B2 | 1/2005 | Yip et al. |
| 6,860,946 B2 | 3/2005 | Hossainy et al. |
| 6,861,088 B2 | 3/2005 | Weber et al. |
| 6,865,810 B2 | 3/2005 | Stinson |
| 6,869,443 B2 | 3/2005 | Buscemi et al. |
| 6,878,160 B2 | 4/2005 | Gilligan et al. |
| 6,887,270 B2 | 5/2005 | Miller et al. |
| 6,887,485 B2 | 5/2005 | Fitzhugh et al. |
| 6,887,510 B2 | 5/2005 | Villareal |
| 6,890,546 B2 | 5/2005 | Mollison et al. |
| 6,890,583 B2 | 5/2005 | Chudzik et al. |
| 6,899,731 B2 | 5/2005 | Li et al. |
| 6,955,723 B2 | 10/2005 | Pacetti et al. |

| | | | | | | |
|---|---|---|---|---|---|---|
| 2001/0007083 A1 | 7/2001 | Roorda | | 2003/0138487 A1 | 7/2003 | Hogan et al. |
| 2001/0014717 A1 | 8/2001 | Hossainy et al. | | 2003/0150380 A1 | 8/2003 | Yoe |
| 2001/0016753 A1 | 8/2001 | Caprio et al. | | 2003/0157241 A1 | 8/2003 | Hossainy et al. |
| 2001/0020011 A1 | 9/2001 | Mathiowitz et al. | | 2003/0158517 A1 | 8/2003 | Kokish |
| 2001/0029351 A1 | 10/2001 | Falotico et al. | | 2003/0171053 A1 | 9/2003 | Sanders |
| 2001/0037145 A1 | 11/2001 | Guruwaiya et al. | | 2003/0185964 A1 | 10/2003 | Weber et al. |
| 2001/0044652 A1 | 11/2001 | Moore | | 2003/0187495 A1 | 10/2003 | Cully et al. |
| 2001/0051608 A1 | 12/2001 | Mathiowitz et al. | | 2003/0190406 A1 | 10/2003 | Hossainy et al. |
| 2002/0002399 A1 | 1/2002 | Huxel et al. | | 2003/0203617 A1 | 10/2003 | Lane et al. |
| 2002/0004060 A1 | 1/2002 | Heublein et al. | | 2003/0207020 A1 | 11/2003 | Villareal |
| 2002/0004101 A1 | 1/2002 | Ding et al. | | 2003/0208259 A1 | 11/2003 | Penhasi |
| 2002/0005206 A1 | 1/2002 | Falotico et al. | | 2003/0209835 A1 | 11/2003 | Chun et al. |
| 2002/0007213 A1 | 1/2002 | Falotico et al. | | 2003/0211230 A1 | 11/2003 | Pacetti et al. |
| 2002/0007214 A1 | 1/2002 | Falotico | | 2003/0215564 A1 | 11/2003 | Heller et al. |
| 2002/0007215 A1 | 1/2002 | Falotico et al. | | 2003/0226833 A1 | 12/2003 | Shapovalov et al. |
| 2002/0009604 A1 | 1/2002 | Zamora et al. | | 2003/0236565 A1 | 12/2003 | DiMatteo et al. |
| 2002/0012741 A1* | 1/2002 | Heinz et al. ............ 427/2.1 | | 2004/0018296 A1 | 1/2004 | Castro et al. |
| 2002/0016625 A1 | 2/2002 | Falotico et al. | | 2004/0029952 A1 | 2/2004 | Chen et al. |
| 2002/0032414 A1 | 3/2002 | Ragheb et al. | | 2004/0047978 A1 | 3/2004 | Hossainy et al. |
| 2002/0032434 A1 | 3/2002 | Chudzik et al. | | 2004/0047980 A1 | 3/2004 | Pacetti et al. |
| 2002/0050220 A1 | 5/2002 | Schueller et al. | | 2004/0052858 A1 | 3/2004 | Wu et al. |
| 2002/0051730 A1 | 5/2002 | Bodnar et al. | | 2004/0052859 A1 | 3/2004 | Wu et al. |
| 2002/0062148 A1 | 5/2002 | Hart | | 2004/0054104 A1 | 3/2004 | Pacetti |
| 2002/0065553 A1 | 5/2002 | Weber | | 2004/0059409 A1* | 3/2004 | Stenzel ............... 623/1.15 |
| 2002/0071822 A1 | 6/2002 | Uhrich | | 2004/0060508 A1 | 4/2004 | Pacetti et al. |
| 2002/0077693 A1 | 6/2002 | Barclay et al. | | 2004/0062853 A1 | 4/2004 | Pacetti et al. |
| 2002/0082679 A1 | 6/2002 | Sirhan et al. | | 2004/0063805 A1 | 4/2004 | Pacetti et al. |
| 2002/0087123 A1 | 7/2002 | Hossainy et al. | | 2004/0071861 A1 | 4/2004 | Mandrusov et al. |
| 2002/0091433 A1 | 7/2002 | Ding et al. | | 2004/0072922 A1 | 4/2004 | Hossainy et al. |
| 2002/0094440 A1 | 7/2002 | Llanos et al. | | 2004/0073298 A1 | 4/2004 | Hossainy |
| 2002/0111590 A1 | 8/2002 | Davila et al. | | 2004/0086542 A1 | 5/2004 | Hossainy et al. |
| 2002/0116050 A1 | 8/2002 | Kocur | | 2004/0086550 A1 | 5/2004 | Roorda et al. |
| 2002/0120326 A1 | 8/2002 | Michal | | 2004/0093077 A1 | 5/2004 | White et al. |
| 2002/0138133 A1 | 9/2002 | Lenz et al. | | 2004/0096504 A1 | 5/2004 | Michal |
| 2002/0142039 A1 | 10/2002 | Claude | | 2004/0098095 A1 | 5/2004 | Burnside et al. |
| 2002/0155212 A1 | 10/2002 | Hossainy | | 2004/0098117 A1 | 5/2004 | Hossainy et al. |
| 2002/0161114 A1 | 10/2002 | Gunatillake et al. | | 2004/0111149 A1 | 6/2004 | Stinson |
| 2002/0165608 A1 | 11/2002 | Llanos et al. | | 2004/0127970 A1 | 7/2004 | Saunders |
| 2002/0176849 A1 | 11/2002 | Slepian | | 2004/0142015 A1 | 7/2004 | Hossainy et al. |
| 2002/0183581 A1 | 12/2002 | Yoe et al. | | 2004/0143317 A1 | 7/2004 | Stinson et al. |
| 2002/0187632 A1 | 12/2002 | Marsh | | 2004/0167610 A1 | 8/2004 | Fleming, III |
| 2002/0188037 A1 | 12/2002 | Chudzik et al. | | 2004/0191405 A1 | 9/2004 | Kerrigan |
| 2002/0188277 A1 | 12/2002 | Roorda et al. | | 2004/0213893 A1 | 10/2004 | Boulais |
| 2003/0003221 A1 | 1/2003 | Zhong et al. | | 2004/0236417 A1 | 11/2004 | Yan et al. |
| 2003/0004141 A1 | 1/2003 | Brown | | 2004/0265475 A1 | 12/2004 | Hossainy |
| 2003/0028243 A1 | 2/2003 | Bates et al. | | 2005/0037052 A1 | 2/2005 | Udipi et al. |
| 2003/0028244 A1 | 2/2003 | Bates et al. | | 2005/0038134 A1 | 2/2005 | Loomis et al. |
| 2003/0031780 A1 | 2/2003 | Chudzik et al. | | 2005/0038497 A1 | 2/2005 | Neuendorf et al. |
| 2003/0032767 A1 | 2/2003 | Tada et al. | | 2005/0043786 A1 | 2/2005 | Chu et al. |
| 2003/0033001 A1 | 2/2003 | Igaki | | 2005/0049693 A1 | 3/2005 | Walker |
| 2003/0036794 A1 | 2/2003 | Ragheb et al. | | 2005/0049694 A1 | 3/2005 | Neary |
| 2003/0039689 A1 | 2/2003 | Chen et al. | | 2005/0054774 A1 | 3/2005 | Kangas |
| 2003/0040712 A1 | 2/2003 | Ray et al. | | 2005/0055044 A1 | 3/2005 | Kangas |
| 2003/0040790 A1 | 2/2003 | Furst | | 2005/0055078 A1 | 3/2005 | Campbell |
| 2003/0054090 A1 | 3/2003 | Hansen | | 2005/0060020 A1 | 3/2005 | Jenson |
| 2003/0055482 A1 | 3/2003 | Schwager et al. | | 2005/0064088 A1 | 3/2005 | Fredrickson |
| 2003/0059520 A1 | 3/2003 | Chen et al. | | 2005/0065501 A1 | 3/2005 | Wallace |
| 2003/0060877 A1 | 3/2003 | Falotico et al. | | 2005/0065545 A1 | 3/2005 | Wallace |
| 2003/0065377 A1 | 4/2003 | Davila et al. | | 2005/0065593 A1 | 3/2005 | Chu et al. |
| 2003/0072868 A1 | 4/2003 | Harish et al. | | 2005/0069630 A1* | 3/2005 | Fox et al. ............... 427/2.24 |
| 2003/0073961 A1 | 4/2003 | Happ | | 2005/0074406 A1 | 4/2005 | Couvillon, Jr. et al. |
| 2003/0083646 A1 | 5/2003 | Sirhan et al. | | 2005/0074544 A1* | 4/2005 | Pacetti et al. ............. 427/2.1 |
| 2003/0083739 A1 | 5/2003 | Cafferata | | 2005/0074545 A1 | 4/2005 | Thomas |
| 2003/0088307 A1 | 5/2003 | Shulze et al. | | 2005/0075714 A1 | 4/2005 | Cheng et al. |
| 2003/0093107 A1 | 5/2003 | Parsonage et al. | | 2005/0079274 A1 | 4/2005 | Palasis et al. |
| 2003/0097088 A1 | 5/2003 | Pacetti | | 2005/0084515 A1 | 4/2005 | Udipi et al. |
| 2003/0097173 A1 | 5/2003 | Dutta | | 2005/0106210 A1 | 5/2005 | Ding et al. |
| 2003/0099712 A1 | 5/2003 | Jayaraman | | 2005/0113903 A1 | 5/2005 | Rosenthal et al. |
| 2003/0100865 A1 | 5/2003 | Santini, Jr. et al. | | | | |
| 2003/0105518 A1 | 6/2003 | Dutta | | FOREIGN PATENT DOCUMENTS | | |
| 2003/0105530 A1 | 6/2003 | Pirhonen | | | | |
| 2003/0113439 A1 | 6/2003 | Pacetti et al. | | CA | 2 007 648 | 4/1991 |
| 2003/0113445 A1 | 6/2003 | Martin | | CA | 1 322 628 | 10/1993 |

| | | | | | | |
|---|---|---|---|---|---|---|
| CA | 1 336 319 | 7/1995 | | GB | 2 370 243 | 6/2002 |
| CA | 1 338 303 | 5/1996 | | GB | 2 384 199 | 7/2003 |
| DE | 042 24 401 | 1/1994 | | JP | SHO49-48336 | 12/1974 |
| DE | 044 07 079 | 9/1994 | | JP | SHO54-1831O | 7/1979 |
| DE | 197 31 021 | 1/1999 | | JP | SHO60-28504 | 7/1985 |
| DE | 199 16 086 | 10/1999 | | JP | 05009726 A | 1/1993 |
| DE | 198 56 983 | 12/1999 | | JP | 21199867 | 5/1994 |
| EP | 0 108 171 | 5/1984 | | JP | HEI8-33718 | 2/1996 |
| EP | 0 144 534 | 6/1985 | | JP | HEI10-151190 | 6/1998 |
| EP | 0 301 856 | 2/1989 | | JP | 2919971 B2 | 7/1999 |
| EP | 0 380 668 | 4/1989 | | JP | 11299901 | 11/1999 |
| EP | 0 351 314 | 1/1990 | | JP | 2001-190687 | 7/2001 |
| EP | 0 364 787 | 4/1990 | | SU | 0872531 | 10/1981 |
| EP | 0 396 429 | 11/1990 | | SU | 0876663 | 10/1981 |
| EP | 0 397 500 | 11/1990 | | SU | 0905228 | 2/1982 |
| EP | 0 464 755 | 1/1992 | | SU | 0790725 | 2/1983 |
| EP | 0 493 788 | 7/1992 | | SU | 1016314 | 5/1983 |
| EP | 0 526 606 | 9/1992 | | SU | 0811750 | 9/1983 |
| EP | 0 514 406 | 11/1992 | | SU | 1293518 | 2/1987 |
| EP | 0 517 075 | 12/1992 | | SU | 1477423 | 5/1989 |
| EP | 0 540 290 | 5/1993 | | WO | WO 89/03232 | 4/1989 |
| EP | 0 553 960 | 8/1993 | | WO | WO 90/01969 | 3/1990 |
| EP | 0 554 082 | 8/1993 | | WO | WO 90/04982 | 5/1990 |
| EP | 0 565 251 | 10/1993 | | WO | WO 90/06094 | 6/1990 |
| EP | 0 578 998 | 1/1994 | | WO | WO 91/11176 | 8/1991 |
| EP | 0 604 022 | 6/1994 | | WO | WO 91/12846 | 9/1991 |
| EP | 0 621 017 | 10/1994 | | WO | WO 91/17744 | 11/1991 |
| EP | 0 623 354 | 11/1994 | | WO | WO 91/17789 | 11/1991 |
| EP | 0 627 226 | 12/1994 | | WO | WO 92/10218 | 6/1992 |
| EP | 0 649 637 | 4/1995 | | WO | WO 93/06792 | 4/1993 |
| EP | 0 665 023 | 8/1995 | | WO | WO 94/09760 | 5/1994 |
| EP | 0 701 802 | 3/1996 | | WO | WO 94/21196 | 9/1994 |
| EP | 0 701 803 | 3/1996 | | WO | WO 95/10989 | 4/1995 |
| EP | 0 709 068 | 5/1996 | | WO | WO 95/11817 | 5/1995 |
| EP | 0 716 836 | 6/1996 | | WO | WO 95/24929 | 9/1995 |
| EP | 0 732 087 | 9/1996 | | WO | WO 95/29647 | 11/1995 |
| EP | 0 832 618 | 9/1996 | | WO | WO 95/33422 | 12/1995 |
| EP | 0 756 853 | 2/1997 | | WO | WO 96/28115 | 9/1996 |
| EP | 0 809 999 | 12/1997 | | WO | WO 96/35516 | 11/1996 |
| EP | 0 832 655 | 4/1998 | | WO | WO 96/40174 | 12/1996 |
| EP | 0 834 293 | 4/1998 | | WO | WO 97/10011 | 3/1997 |
| EP | 0 850 604 | 7/1998 | | WO | WO 97/45105 | 12/1997 |
| EP | 0 850 651 | 7/1998 | | WO | WO 97/46590 | 12/1997 |
| EP | 0 875 218 | 11/1998 | | WO | WO 98/04415 | 2/1998 |
| EP | 0 879 595 | 11/1998 | | WO | WO 98/07390 | 2/1998 |
| EP | 0 897 701 | 2/1999 | | WO | WO 98/08463 | 3/1998 |
| EP | 0 910 584 | 4/1999 | | WO | WO 98/17331 | 4/1998 |
| EP | 0 923 953 | 6/1999 | | WO | WO 98/20863 | 5/1998 |
| EP | 0 953 320 | 11/1999 | | WO | WO 98/23228 | 6/1998 |
| EP | 0 970 711 | 1/2000 | | WO | WO 98/32398 | 7/1998 |
| EP | 0 972 498 | 1/2000 | | WO | WO 98/36784 | 8/1998 |
| EP | 0 974 315 | 1/2000 | | WO | WO 99/01118 | 1/1999 |
| EP | 0 982 041 | 3/2000 | | WO | WO 99/03515 | 1/1999 |
| EP | 1 023 879 | 8/2000 | | WO | WO 99/16386 | 4/1999 |
| EP | 1 034 752 | 9/2000 | | WO | WO 99/38546 | 8/1999 |
| EP | 1 075 838 | 2/2001 | | WO | WO 99/42147 | 8/1999 |
| EP | 1 103 234 | 5/2001 | | WO | WO 99/63981 | 12/1999 |
| EP | 1 192 957 | 4/2002 | | WO | WO 00/02599 | 1/2000 |
| EP | 1 273 314 | 1/2003 | | WO | WO 00/12147 | 3/2000 |
| EP | 0 869 847 | 3/2003 | | WO | WO 00/18446 | 4/2000 |
| EP | 0 941 072 | 1/2004 | | WO | WO 00/64506 | 11/2000 |
| FR | 2 753 907 | 4/1998 | | WO | WO 01/01890 | 1/2001 |
| GB | 2 247 696 | 3/1992 | | WO | WO 01/15751 | 3/2001 |
| GB | 2 316 086 | 1/2000 | | WO | WO 01/17459 | 3/2001 |
| GB | 2 316 342 | 1/2000 | | WO | WO 01/17577 | 3/2001 |
| GB | 2 333 975 | 1/2000 | | WO | WO 01/43727 | 6/2001 |
| GB | 2 336 551 | 1/2000 | | WO | WO 01/45763 | 6/2001 |
| GB | 2 356 586 | 5/2001 | | WO | WO 01/49338 | 7/2001 |
| GB | 2 356 587 | 5/2001 | | WO | WO 01/51027 | 7/2001 |
| GB | 2 333 474 | 6/2001 | | WO | WO 01/52772 | 7/2001 |
| GB | 2 334 685 | 6/2001 | | WO | WO 01/57144 | 8/2001 |
| GB | 2 356 585 | 7/2001 | | WO | WO 01/74414 | 10/2001 |
| GB | 2 374 302 | 8/2001 | | WO | WO 01/91918 | 12/2001 |

| | | |
|---|---|---|
| WO | WO 02/03890 | 1/2002 |
| WO | WO 02/26162 | 4/2002 |
| WO | WO 02/34311 | 5/2002 |
| WO | WO 02/47731 | 6/2002 |
| WO | WO 02/49771 | 6/2002 |
| WO | WO 02/056790 | 7/2002 |
| WO | WO 02/058753 | 8/2002 |
| WO | WO 02/087550 | 11/2002 |
| WO | WO 02/102283 | 12/2002 |
| WO | WO 03/000308 | 1/2003 |
| WO | WO 03/007918 | 1/2003 |
| WO | WO 03/007919 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/061841 | 7/2003 |
| WO | WO 03/072084 | 9/2003 |
| WO | WO 03/072086 | 9/2003 |
| WO | WO 03/080147 | 10/2003 |
| WO | WO 03/082368 | 10/2003 |
| WO | WO 04/000383 | 12/2003 |
| WO | WO 2004/009145 | 1/2004 |
| WO | WO 2004/017947 | 3/2004 |
| WO | WO 2004/017976 | 3/2004 |
| WO | WO 2004/023985 | 3/2004 |
| WO | WO 2004/024339 | 3/2004 |

OTHER PUBLICATIONS

U.S. Appl. No. 09/997,390, filed Nov. 30, 2001, Pacetti.
U.S. Appl. No. 10/040,538, filed Dec. 28, 2001, Pacetti et al.
U.S. Appl. No. 10/255,913, filed Sep. 26, 2002, Tang et al.
U.S. Appl. No. 10/262,161, filed Sep. 30, 2002, Pacetti.
U.S. Appl. No. 10/266,479, filed Oct. 8, 2002, Hossainy.
U.S. Appl. No. 10/304,669, filed Nov. 25, 2002, Madriaga et al.
U.S. Appl. No. 10/317,435, filed Dec. 11, 2002, Hossainy et al.
U.S. Appl. No. 10/322,255, filed Dec. 17, 2002, Chen et al.
U.S. Appl. No. 10/319,042, filed Dec. 12, 2002, Van Sciver et al.
U.S. Appl. No. 10/330,412, filed Dec. 27, 2002, Hossainy et al.
U.S. Appl. No. 10/376,027, filed Feb. 26, 2003, Kokish et al.
U.S. Appl. No. 10/438,378, filed May 15, 2003, Esbeck et al.
U.S. Appl. No. 10/660,853, filed Sep. 12, 2003, Pacetti et al.
U.S. Appl. No. 10/729,551, filed Dec. 5, 2003, Pacetti.
U.S. Appl. No. 10/729,728, filed Dec. 5, 2003, Pacetti.
U.S. Appl. No. 10/409,410, filed Apr. 7, 2003, Pacetti.
U.S. Appl. No. 10/750,312, filed Dec. 30, 2003, Desnoyer et al.
U.S. Appl. No. 10/805,047, filed Mar. 18, 2004, Yip et al.
U.S. Appl. No. 10/813,845, filed Mar. 30, 2004, Pacetti.
U.S. Appl. No. 10/817,642, filed Apr. 2, 2004, Kerrigan.
U.S. Appl. No. 11/193,849, filed Jul. 28, 2005, Harold et al.
U.S. Appl. No. 11/222,052, filed Sep. 7, 2005, Pacetti et al.
U.S. Appl. No. 11/222,053, filed Sep. 7, 2005, Pacetti et al.
U.S. Appl. No. 11/233,991, filed Sep. 22, 2005, Hossainy.
U.S. Appl. No. 10/439,415, filed May 15, 2003, Perng.
U.S. Appl. No. 10/602,487, filed Jun. 23, 2003, Castro et al.
U.S. Appl. No. 10/630,250, filed Jul. 30, 2003, Pacetti et al.
U.S. Appl. No. 10/676,545, filed Sep. 30, 2003, Fox et al.
U.S. Appl. No. 10/680,905, filed Oct. 7, 2003, Pacetti et al.
U.S. Appl. No. 10/738,704, filed Dec. 16, 2003, Pacetti et al.
U.S. Appl. No. 10/741,214, filed Dec. 19, 2003, Pacetti.
U.S. Appl. No. 10/747,996, filed Dec. 29, 2003, Chen et al.
U.S. Appl. No. 10/750,139, filed Dec. 30, 2003, DesNoyer et al.
U.S. Appl. No. 10/805,036, filed Mar. 16, 2004, Pacetti.
U.S. Appl. No. 10/816,072, filed Mar. 31, 2004, Dugan et al.
U.S. Appl. No. 10/824,754, filed Apr. 15, 2004, Perng.
U.S. Appl. No. 10/833,902, filed Apr. 27, 2004, Chen et al.
U.S. Appl. No. 10/835,229, filed Apr. 28, 2004, Prabhu et al.
U.S. Appl. No. 10/835,656, filed Apr. 30, 2004, Tang et al.
U.S. Appl. No. 10/851,411, filed May 20, 2004, Chen.
U.S. Appl. No. 10/855,294, filed May 26, 2004, Pacetti et al.
U.S. Appl. No. 10/877,527, filed Jun. 24, 2004, Yan et al.
U.S. Appl. No. 10/897,244, filed Jul. 21, 2004, Hossainy et al.

U.S. Appl. No. 10/928,587, filed Aug. 26, 2004, Hossainy et al.
U.S. Appl. No. 10/931,853, filed Aug. 31, 2004, Hossainy et al.
U.S. Appl. No. 10/932,364, filed Aug. 31, 2004, Foreman et al.
U.S. Appl. No. 11/015,313, filed Dec. 16, 2004, Pacetti et al.
U.S. Appl. No. 11/093,166, filed Mar. 28, 2005, Kerrigan.
U.S. Appl. No. 11/115,631, filed Apr. 26, 2005, Chen.
U.S. Appl. No. 11/119,020, filed Apr. 29, 2005, Hossainy et al.
U.S. Appl. No. 11/187,467, filed Jul. 22, 2005, Desnoyer et al.
Anonymous, *Bioabsorbable stent mounted on a catheter having optical coherence tomography capabilities*, Research Disclosure, pp. 1159-1162 (Sep. 2004).
Anonymous, *Capillary Rise of Liquid in Different Vanes Under Variable Residual Acceleration*, http://www.zarm.uni-bremen.de/2forschung/grenzph/isoterm/cap_rise/kapst_en.htm,
ZARM—University of Bremen, printed Jun. 25, 2003, 2 pages.
Anonymous, *Cardiologists Draw—Up The Dream Stent*, Clinica 710, pp. 15 (Jun. 17, 1996), http://www.dialogweb.com/cgi/document?req=1061848202959, printed Aug. 25, 2003, 2 pages.
Anonymous, *Heparin-coated stents cut complications by 30%*, Clinica 732, pp. 17 (Nov. 18, 1996), http://www.dialogweb.com/cgi/document?req=1061847871753, printed Aug. 25, 2003, 2 pages.
Anonymous, *Rolling Therapeutic Agent Loading Device for Therapeutic Agent Delivery or Coated Stent* (Abstract 434009), Res. Disclos. pp. 974-975 (Jun. 2000).
Anonymous, *Stenting Continues to Dominate Cardiology*, http://www.dialogweb.com/cgi/document?req=1061848017752, Clinica vol. 720, pp. 22 (Sep. 2, 1996), printed Aug. 25, 2003, 2 pages.
Anonymous, *The Wicking Well System*, http://www.decorative.com/wickinq.html, printed Jun. 24, 2003, 1 page.
Ansari, *End-to-End Tubal Anastomosis Using an Absorbable Stent*, Fertility and Sterility, vol. 32, No. 2, pp. 197-201 (Aug. 1979).
Ansari, *Tubal Reanastomosis Using Absorbable Stent*, International Journal of Fertility, vol. 23, No. 4, pp. 242-243 (1978).
Aoyagi et al., *Preparation of cross-linked aliphatic polyester and application to thermo-responsive material*, Journal of Controlled Release 32, pp. 87-96 (1994).
Barath et al., *Low Dose of Antitumor Agents Prevents Smooth Muscle Cell Proliferation After Endothelial Injury*, JACC vol. 3, No. 2, pp. 252A (Feb. 1989).
Barbucci et al., *Coating of commercially available materials with a new heparinizable Material*, Journal of Biomedical Materials Research, vol. 25, pp. 1259-1274 (1991).
Beach et al., *Xylylene Polymers*, Encyclopedia of Polymer Science and Engineering, vol. 17, 2nd Edition, pp. 990-1025 (1989).
Boston Scientific, *Express $^2$™ Coronary Stent System*, http://www.bostonscientific.com/med_specialty/deviceDetail.jsp?task=tskBasicDevice.jsp&sectionId=4&re lId=2,74,75,76&deviceId=11001&uniqueId=MPDB1180&clickType=endeca,
printed Aug. 8, 2005, 1 page.
Bull, *Parylene Coating for Medical Applications*, Medical Product Manufacturing News, 2 pages (Mar. 1993).
Casper et al., *Fiber-Reinforced Absorbable Composite for Orthopedic Surgery*, Polymeric Materials Science and Engineering, vol. 53, pp. 497-501(1985).
Charlson et al., *Temperature Selective Deposition of Parylene-C*, IEEE Transactions of Biomedical Engineering, vol. 39, No. 2, pp. 202-206 (Feb. 1992).
Chen et al., *The Kinetics of Wicking of Liquid Droplets into Yarns*, submitted to the Textile Research Journal, pp. 1-30 (Apr. 2001).
Chung et al., *Inner core segment design for drug delivery control of thermo-responsive polymeric micelles*, Journal of Controlled Release, vol. 65, pp. 93-103 (2000).
Crowe et al., *Absorption and Intestinal Metabolism of SDZ-RAD and Rapamycin in Rats*, Drug Metabolism and Disposition, vol. 27, No. 5, pp. 627-632 (1999).
De Scheerder et al., *Biocompatibility of polymer-coated oversized metallic stents implanted in normal porcine coronary arteries*, Atherosclerosis, vol. 114, pp. 105-114 (1995).
Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9, No. 2, pp. 111-130 (Mar./Apr. 1996).

Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9, No. 6, pp. 495-504 (Nov./Dec. 1996).

Detweiler et al., *Sutureless Anastomosis of the Small Intestine and the Colon in Pigs Using an Absorbable Intraluminal Stent and Fibrin Glue*, Journal of Investigative Surgery, vol. 8, No. 2, pp. 129-140 (Mar. 1995).

Detweiler et al., *Sutureless Cholecystojejunostomy in Pigs Using an Absorbable Intraluminal Stent and Fibrin Glue*, Journal of Investigative Surgery, vol. 9, No. 1, pp. 13-26 (Jan./Feb. 1996).

Dev et al., *Kinetics of Drug Delivery to the Arterial Wall Via Polyurethane-Coated Removable Nitinol Stent: Comparative Study of Two Drugs*, Catheterization and Cardiovascular Diagnosis, vol. 34, pp. 272-278 (1995).

Devanathan et al., *Polymeric Conformal Coatings for Implantable Electronic Devices*, IEEE Transactions on Biomedical Engineering, vol. BME-27, No. 11, pp. 671-675 (1980).

Dichek et al., *Seeding of Intravascular Stents with Genetically Engineered Endothelial Cells*, Circulation, vol. 80, No. 5, pp. 1347-1353 (Nov. 1989).

Dreyer et al., *Critical Velocities in Open Capillary Flows*, pp. 604-609 (no date).

Duerig et al., *A comparison of balloon-and self-expanding stents*, Min. Invas. Ther. & Allied Technol., vol. 11, No. 4, pp. 173-178 (2002).

Dutkiewicz, *Some Advances in Nonwoven Structures for Absorbency, Comfort and Aesthetics*, AUTEX Research Journal, vol. 2, No. 3, pp. 153-165 (Sep. 2002).

EFD, *780S Series Spray Valves VALVEMATE™ 7040 Controller Operating Manual*, 24 pages (2002).

Eigler et al., *Local Arterial Wall Drug Delivery from a Polymer Coated Removable Metallic Stent: Kinetics, Distribution, and Bioactivity of Forskolin*, JACC, vol. 4A, pp. 701-701, Abstract (Feb. 1994).

Elbert et al., *Conjugate Addition Reactions Combined with Free-Radical Cross-Linking for the Design of Materials for Tissue Engineering*, Biomacromolecules, vol. 2, pp. 430-441 (2001).

Erickson et al., *Numerical Simulations of Capillary-Driven Flows in Nonuniform Cross-Sectional Capillaries*, Journal of Colloid and Interface Science, vol. 250, pp. 422-430 (2002).

Eskin et al., *Growth of Cultured Calf Aortic Smooth Muscle Cells on Cardiovascular Prosthetic Materials*, J. Biomed. Mater. Res. vol. 10, pp. 113-122 (1976).

Eskin et al., *Tissue Cultured Cells: Potential Blood Compatible Linings for Cardiovascular Prostheses*, Polymer Science and Technology, vol. 14, pp. 143-161 (no date).

Fischell et al., *Low-Dose, β-Particle Emission from 'Stent' Wire Results in Complete, Localized Inhibition of Smooth Muscle Cell Proliferation*, Circulation, vol. 90, No. 6, pp. 2956-2963 (Dec. 1994).

Fischell et al., *The Bx Velocity™ Stent*, 5 pages, Biocompatibles Ltd. (2001).

Forrester et al., *A Paradigm for Restenosis Based on Cell Biology: Clues for the Development of New Preventive Therapies*; J. Am. Coll. Cardio. 1991; 17:758-769.

Gengenbach et al., *Evolution of the Surface Composition and Topography of Perflurinated Polymers Following Ammonia-Plasma Treatment*, Plasma Surface Modifications of Polymers, pp. 123-146 (1994).

Gercken et al., *Results of the Jostent Coronary Stent Graft Implantation in Various Clinical Settings: Procedural and Follow-Up Results*, vol. 56, No. 3, pp. 353-360 (2002).

Gölander et al., *RF-Plasma-Modified Polystyrene Surfaces for Studying Complement Activation*, J. Biomater. Sci. Plymer Edn., vol. 4, No. 1 pp. 25-30 (1992).

Hahn et al., *Biocompatibility of Glow-Discharge-Polmerized Films and Vacuum-Deposited Parylene*, Journal of Applied Polymer Science: Applied Polymer Symposium 38, 55-64 (1984).

Hahn et al., *Glow Discharge Polymers as Coatings for Implanted Devices*, John M. Dalton Research Center, University of Missouri-Columbia and the Graduate Center for Materials Research, pp. 109-113 (1981).

He et al., *Assessment of Tissue Blood Flow Following Small Artery Welding with an Intraluminal Dissolvable Stent*, Microsurgery, vol. 19, No. 3, pp. 148-152 (1999).

Hehrlein et al., *Low-Dose Radioactive Endovascular Stents Prevent Smooth Muscle Cell Proliferation and Neointimal Hyperplasia in Rabbits*, Circulation, vol. 92, No. 6, pp. 1570-1575 (Sep. 15, 1995).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol., vol. 3, pp. 197-199 (1998).

Hollahan et al., *Attachment of Amino Groups to Polymer Surfaces by Radiofrequency Plasmas*, Journal of Applied Polymer Science, vol. 13, pp. 807-816 (1969).

Huang et al., *Biodegradable Polymers Derived from Aminoacids*, Macromol. Symp. 144, 7-32 (1999).

Illbruck Sealant Systems, *Application: Window and Perimeter Silicone*, http://www.willseal.com/usa/produktuebersicht/dichtstoffe/perwindow/verlege_anleitung...., printed Nov. 29, 2004 (3 pages).

Impulse Jetting, *About Us*, http://www.impulsejetting.com/about.html, printed Dec. 18, 2000, 1 page.

Impulse Jetting, *Our Technology*, http://www.impulsejetting.com/tech1.html, printed Dec. 18, 2000, 1 page.

Inagaki et al., *Hydrophilic Surface Modification of Polyethylene by No-Plasma Treatment*, Adhesion Sci. Technol., vol. 4, No. 2, pp. 99-107 (1990).

Inoue et al., *An AB block copolymer of oligo(methyl methacrylate) and poly(acrylic acid) for micellar delivery of hydrophobic drugs*, Journal of Controlled Release, vol. 51, pp. 221-229 (1998).

International Search Report and Written Opinion of WIPO Application No. WIPO/US2004/026137 filed Aug. 11, 2004 (Jan. 31, 2005).

*International Search Report and Written Opinion*, dated Mar. 1, 2005 for PCT Application No. PCT/US2004/031185, filed Sep. 22, 2004 (14 pages).

Itabashi et al., *Electroless Deposited CoWB for Copper Diffusion Barrier Metal*, International Interconnect Technology Conference, pp. 285-287 (2002).

John Ritchie Production Group, *Production of Stents* (presentation), 15 pages (Apr. 24, 2003).

Kataoka et al., *Block Copolymer Micelles as Vehicles for Drug Delivery*, Journal of Controlled Release vol. 24, pp. 119-132 (1993).

Katsarava et al., *Amino Acid-Based Bioanalogous Polymers. Synthesis and Study of Regular Poly(ester amide)s Based on Bis(α-amino acid)α,ω-Alkylene Diesters, and Aliphatic Dicarbolic Acids*, Journal of Polymer Science, Part A: Polymer Chemistry, vol. 37, 391-407 (1999).

Kawai et al., *Physiologically Based Pharmacokinetics of Cyclosporine A: Extension to Tissue Distribution Kinetics in Rats and Scale-up to Human*, The Journal of Pharmacology and Experimental Therapeutics, vol. 287, No. 2, pp. 457-468 (1998).

Kelley et al., *Totally Resorbable High-Strength Composite Material*, Advances in Biomedical Polymers, vol. 35, pp. 75-85 (1987).

Kim, *Solid State Sintering*, AMSE 604 Solid State Reactions and Sintering, Electroceramic laboratory in Dept. of Materials Science & Engineering, POSTECH, Pohang University of Science and Technology (20 pages).

Klocke et al, *How Soil Holds Water* (G90-964), http://ianrpubs.unl.edu/fieldcrops/g964.htm, printed Apr. 6, 2004, 9 pages.

Konopka, *In-Plane Moisture Transport in Nonwovens*, Nonwovens Cooperative Research Center, NC State University, 56 pages (no date).

Kovarik et al., *Pharmacokinetic and Pharmacodynamic Assessments of HMG-CoA Reductase Inhibitors When Coadministered with Everolimus*, Journal of Clinical Pharmacology, vol. 42, pp. 222-228 (2002).

Kubies et al., *Microdomain Structure in polylactide-block-poly(ethylene oxide) copolymer films*, Biomaterials, vol. 21, pp. 529-536 (2000).

Kutryk et al., *Coronary Stenting: Current Perspectives, a companion to the Handbook of Coronary Stents*, 16 pages (1999).

Lambert et al., *Localized Arterial Wall Drug Delivery From a Polymer-Coated Removable Metallic Stent*, Circulation, vol. 90, No. 2, pp. 1003-1011 (Aug. 1994).

Lemos et al., *Coronary Restenosis After Sirolimus-Eluting Stent Implantation*, Circulation, vol. 108, No. 3, pp. 257-260 (Jul. 22, 2003).

Levy et al., *Strategies for Treating Arterial Restenosis Using Polymeric Controlled Release Implants*, Biotechnology and Bioactive Polymers, pp. 259-268 (1994).

Liermann et al., *Prophylactic Endovascular Radiotherapy to Prevent Intimal Hyperplasia after Stent Implantation in Femoropopliteal Arteries*, CardioVascular and Interventional Radiology, vol. 17, pp. 12-16 (1994).

Liu et al., *Drug Release Characteristics of Unimolecular Polymeric Micelles*, Journal of Controlled Release, vol. 68, pp. 167-174 (2000).

Loeb et al., *Parylene as a Chronically Stable, Reproducible Microelectrode Insulator*, IEEE Transactions on Biomedical Engineering, pp. 121-128 (Mar. 1977).

Loh et al., *Plasma Enhanced Parylene Deposition*, Antec, pp. 1099-1103 (1991).

Machine Solutions, *FFS700 MSI Balloon Form/Fold/Set Equipment (PTCA), FFS800 MSI Balloon Form/Fold/Set Equipment (PTA)*, http://machinesolutions.org/ffs7_8.html, printed Nov. 21, 2003 (2 pgs.).

Machine Solutions, *SC700 MSI Stent Crimping Equipment (PTCA), SC800 MSI Stent Crimping Equipment (PTA)*, http://www.machinesolutions.org/sc7_8.html, printed Nov. 21, 2003, 2 pages.

Malik et al., *Development of an Energetic Ion Assisted Mixing and Deposition Process for $TIN_x$ and Diamondlike Carbon Films, Using a Co-axial Geometry in Plasma Source Ion Implantation*, J. Vac. Sci. Technol. A, vol. 15, No. 6, pp. 2875-2879 (Nov./Dec. 1997).

Malik et al., *Overview of plasma source ion implantation research at University of Wisconsin-Madison*, J. Vac. Sci. Technol. B, No. 12, vol. 2, pp. 843-849 (Mar./Apr. 1994).

Malik et al., *Sheath dynamics and dose analysis for planar targets in plasma source ion implantation*, Plasma Sources Sci. Technol. vol. 2, pp. 81-85 (1993).

Marconi et al., *Covalent bonding of heparin to a vinyl copolymer for biomedical applications*, Biomaterials, vol. 18, No. 12, pp. 885-890 (1997).

Martin et al., *Enhancing the biological activity of immobilized osteopontin using a type-1 collagen affinity coating*, J. Biomed. Mater. Res., vol. 70A, pp. 10-19 (May 14, 2004).

Matsumaru et al., *Embolic Materials for Endovascular Treatment of Cerebral Lesions*, J. Biomater. Sci. Polymer Edn., vol. 8, No. 7, pp. 555-569 (1997).

Mauduit et al., *Hydrolytic degradation of films prepared from blends of high and low molecular weight poly(DL-lactic acid)s*, J. Biomed. Mater. Res., vol. 30, pp. 201-207 (1996).

Middleton et al., *Synthetic biodegradable polymers as orthopedic devices*, Biomaterials, vol. 21, pp. 2335-2346 (2000).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull., vol. 33, No. 6, pp. 2490-2498 (1985).

Miyazawa et al., *Effects of Pemirolast and Tranilast on Intimal Thickening After Arterial Injury in the Rat*, J. Cardiovasc. Pharmacol., vol. 30, No. 2, pp. 157-162 (1997).

Moody, *Vacuum Coating Ultrasonic Transducers*, 1 page, Sensors (Dec. 1993).

Muller et al., *Advances in Coronary Angioplasty: Endovascular Stents*, Coronary Artery Disease, vol. 1, No. 4., pp. 438-448 (Jul./Aug. 1990).

Neimark et al., *Hierarchical Pore Structure and Wetting Properties of Single-Wall Carbon Nanotube Fibers*, Nano Letters, vol. 3, No. 3, pp. 419-423 (2003).

Nichols et al., *Electrical Insulation of Implantable Devices by Composite Polymer Coatings*, ISA Transactions, vol. 26, No. 4, pp. 15-18 (1987).

Nordrehaug et al., *A Novel Biocompatible Coating Applied to Coronary Stents*, EPO Heart Journal 14, p. 321 (P1694), Abstr. Suppl. (1993).

Nova Tran™ Custom Coating Services, *Parylene Conformal Coating*, 8 pages (no date).

Ohsawa et al., *Preventive Effects of an Antiallergic Drug, Pemirolast Potassium, on Restenosis After Percutaneous Transluminal Coronary Angioplasty*, American Heart Journal, vol. 136, No. 6, pp. 1081-1087 (Dec. 1998).

Ozaki et al., *New Stent Technologies*, Progress in Cardiovascular Diseases, vol. XXXIX, No. 2, pp. 129-140 (Sep./Oct. 1996).

Pechar et al., *Poly(ethylene glycol) Multiblock Copolymer as a Carrier of Anti-Cancer Drug Doxorubicin*, Bioconjucate Chemistry vol. 11, No. 2, pp. 131-139 (Mar./Apr. 2000).

Peng et al., *Role of polymers in improving the results of stenting in coronary arteries*, Biomaterial, vol. 17, pp. 685-694 (1996).

Peuster et al., *A novel approach to temporary stenting: degradable cardiovascular stents produced from corrodible metal-results 6-18 months after implantation into New Zealand white rabbits*, Heart vol. 86, pp. 563-569 (2001).

Pietrzak et al., *Bioabsorbable Fixation Devices: Status for the Craniomaxillofacial Surgeon*, Journal of Craniofacial Surgery, vol. 8, No. 2, pp. 92-96 (1997).

Pietrzak et al., *Bioresorbable Implants—Practical Considerations*, Bone, vol. 19, No. 1, Supplement, pp. 109S-119S (Jul. 1996).

Poncin-Epaillard et al., *Reactivity of a Polypropylene Surface Modified in a Nitrogen Plasma*, Plasma Surface Modification of Polymers pp. 167-180 (1994).

Prabhu, *Computational Modeling in Stent-based Drug Delivery*, Business Briefing: Medical Device Manufacturing & Technology, 4 pages (2004).

Redman, *Clinical Experience with Vasovasostomy Utilizing Absorbable Intravasal Stent*, Urology, vol. XX, No. 11, pp. 59-61 (Jul. 1982).

Refracton Techonolgies, Corp., *Refractron Advanced Porous Ceramic Product Capabilities*, http://www.refractron.com/ecom/sp/cat=Product+Information, printed Apr. 6, 2004, 3 pages.

Refractron Technologies Corp., http://www.refractron.com/ecom/sp/cat=Custom+Applications, printed Jun. 24, 2003, 1 page.

Rust et al., *The Effect of Absorbable Stenting on Postoperative Stenosis of the Surgically Enlarged Maxillary Sinus Ostia in a Rabbit Animal Model*, Archives of Otolaryngology, Head and Neck Surgery, vol. 122, pp. 1395-1397 (Dec. 1996).

Sadhir et al., *The Adhesion of Glow-Discharge Polymers, Silastic and Parylene to Implantable Platinum Electrodes: Results of Tensil Pull tests After Exposure to Isotonic Sodium Chloride*, Biomaterials, vol. 2, pp. 239-243 (Oct. 1981).

Saotome, et al., *Novel Enzymatically Degradable Polymers Comprising α-Amino Acid, 1,2-Ethanediol, and Adipic Acid*, Chemistry Letters, pp. 21-24, (1991).

Schatz, *A View of Vascular Stents*, Circulation, vol. 79, No. 2, pp. 445-457 (Feb. 1989).

Scheuer et al., *Model of plasma source ion implantation in planar, cylindrical, and spherical geometries*, J. Appl. Phys., vol. 67, No. 3, pp. 1241-1245 (Feb. 1990).

Schmidt et al., *Long-term Implants of Parylene-C Coated Microelectrodes*, Medical & Biological Engineering & Computing, pp. 96-101 (Jan. 1988).

Serkova et al., *Tissue Distribution and Clinical Monitoring of the Novel Macrolide Immunosuppressant SDZ-RAD and its Metabolites in Monkey Lung Transplant Recipients: Interaction with Cyclosporine*, The Journal of Pharmacology and Experimental Therapeutics, vol. 294, No. 1, pp. 323-332 (2000).

Serruys et al., *I Like the Candy, I Hate the Wrapper; the $^{32}P$ Radioactive Stent*, Circulation, vol. 101, pp. 3-7 (Jan. 2000).

Shamim et al., *Measurement of electron emission due to energetic ion bombardment in plasma source ion implantation*, J. Appl. Phys., vol. 70, No. 9, pp. 4756-4759 (Nov. 1991).

Shamim et al., *Measurements of Spatial and Temporal Sheath Evolution for Spherical and Cylindrical Geometries in Plasma Source Ion Implantation*, J. Appl. Phys., vol. 69, No. 5, pp. 2904-2908 (Mar. 1991).

Shigeno, *Prevention of Cerebrovascular Spasm by Bosentan, Novel Endothelin Receptor*, Chemical Abstract 125:21230 (1996).

Sono Tek Corporation, *AccuMist™ for Single Stent Coating Applications*, http://www.sono-tek.com/biomedical/accumist_stent.html, printed Aug. 2, 2005, 3 pages.

Sono Tek Corporation, *MediCoat™ DES 1000, Benchtop Stent Coating System*, http://www.sono-tek.com/biomedical/medicoat_standalone.html, printed Aug. 2, 2005, 4 pages.

Sono Tek Corporation, *MicroMist for Stent Coating*, http://www.sono-tek.com/biomedical/micromist_stent.html, printed Aug. 2, 2005, 3 pages.

Spagnuolo et al., *Gas 1 is induced by VE-cadherin and vascular endothelial growth factor and inhibits endothelial cell apoptosis*, Blood, vol. 103, No. 6, pp. 3005-3012 (2004).

Specialty Coating Systems, Inc., *The Parylene Press*, 4 pages (Summer 1993).

Specialty Coating Systems, Inc., *The Parylene Press*, 6 pages (Spring 1993).

Specialty Coating Systems, Inc., *The Parylene Press*, 7 pages (Winter 1992).

Tamai et al., *Initial and 6-Month Results of Biodegradable Poly-I-Lactic Acid Coronary Stents in Humans*, Circulation, vol. 102, pp. 399-404 (2000).

Trident, Inc., http://www.tridentintl.com/subbody.html, printed Dec. 18, 2000, 1 page.

Trident, Inc., *Product Lines*, http://www.tridentintl.com/products-apps/ultrajet.html, printed Dec. 18, 2000, 3 pages.

Tsuji et al., *Biodegradable Polymeric Stents*, Current Interventional Cardiology Reports vol. 3, pp. 10-17 (2001).

Union Carbide Adhesion Promoters, *Union Carbide A-174 Silane*, 5 pages (Jan. 1968).

Union Carbide, *Abrasion Resistance of Parylene and Other Conformal Circuit Board Coatings*, Parylene Products, No. 4, 13 pages (Oct. 1977).

Union Carbide, *Adhesion Promotion Systems for Parylene*, Parylene Products, No. 15, Revision 1, 8 pages (Oct. 1977).

Union Carbide, *Adhesion Promotion Systems for Parylene*, Technology Letter, No. 15, 13 pages (Oct. 1975).

Union Carbide, *Evaluation of Parylene and Other Pellicles as Beam Splitters*, Parylene Products, No. 8, Edited, 19 pages (Oct. 1977).

Union Carbide, *Fluorescent Parylene Coatings*, Parylene Products, No. 7 Revision 1, 8 pages (Oct. 1977).

Union Carbide, *Fluorescent Parylene Coatings*, Technology Letter, No. 7, 8 pages (Oct. 1973).

Union Carbide, *Mechanical Protection Criteria for Thin Conformal Coatings*, Parylene Products, No. 3, 21 pages (Oct. 1977).

Union Carbide, *Method for Repair and Patching of Parylene Coated Printed Circuit Boards*, Parylene Products, No. 2 Revision 1, 9 pages (Oct. 1977).

Union Carbide, *Microencapsulation by Vapor Deposition*, Parylene Products, No. 6, 12 pages (Oct. 1977).

Union Carbide, *MIL I 46058, Qualification of Parylene N, C, and D*, Parylene Products, No. 1 Revision 2, 8 pages (Oct. 1977).

Union Carbide, *Parylene Bibliography*, Parylene Products, No. 5, Revision 4, 17 pages (Jan. 18, 1982).

Union Carbide, *Parylene Conformal Coatings for Hybrid Microelectronics*, Parylene Products, No. 9, 23 pages (Oct. 1973).

Union Carbide, *Parylene Pellicles for Space Applications*, Parylene Products, No. 10, 50 pages (Oct. 1977).

Union Carbide, *Parylene Pyrolysis Kinetics*, Parylene Products, No. 11, 12 pages (Oct. 1977).

Union Carbide, *Parylene Pyrolysis Kinetics*, Technology Letter, No. 11, 12 pages (May 1974).

Union Carbide, *Parylene Removal with Oxygen Plasmas*, Parylene Products, No. 18, 7 pages (Aug. 1977).

Union Carbide, *Printed Circuit Board Masking Techniques for Use with Parylene*, No. 14, Revision 1, 11 pages (Oct. 1977).

Union Carbide, *Solvent Resistance of the Parylenes*, Parylene Products, No. 12, Revision 1, 5 pages (Oct. 1977).

Union Carbide, *The Selective Removal of Parylene by Plasma Etching*, No. 13, Revision 1, 7 pages (Oct. 1977).

Union Carbide, *Thermal Endurance of the Parylenes in Air*, Parylene Products, No. 16, 4 pages (Mar. 1976).

Union Carbide, *Vapor Phase Adhesion Promotion Systems*, Parylene Products, No. 17, Revision 1, 11 pages (Oct. 1977).

van Beusekom et al., *Coronary Stent Coatings*, Coronary Artery Disease, vol. 5, No. 7, pp. 590-596 (Jul. 1994).

van der Giessen et al., *"Edge Effect" of $^{32}P$ Radioactive Stents is Caused by the Combination of Chronic Stent Injury and Radioactive Dose Falloff*, Circulation, vol. 104, pp. 2236-2241 (Oct. 30, 2001).

Van Iseghem, *Important Concepts on Coating Plastics From a Formulator's Perspective*, Modern Paint and Coatings, pp. 30-38 (Feb. 1998).

Vapor Inc., *Vapore-Jet™ Capillary Pump—How it Works*, http://www.vapore.com/tech_howto.htm, printed Aug. 13, 2003, 2 pages.

Völkel et al., *Targeting of immunoliposomes to endothelial cells using a single-chain Fv fragment directed against human endoglin (CD105)*, Biochemica et Biophysica Acta, vol. 1663, pp. 158-166 (Apr. 15, 2004).

von Recum et al., *Degradation of polydispersed poly(L-lactic acid) to modulate lactic acid release*, Biomaterials, vol. 16, pp. 441-445 (1995).

Wiesendanger et al., *Contributions of Scanning Probe Microscopy and Spectroscopy to the Investigation and Fabrication of Nanometer-Scale Structures*, J. Vac. Sci. Technol. B, vol. 12, No. 2, pp. 515-529 (Mar./Apr. 1994).

Wilensky et al., *Methods and Devices for Local Drug Delivery in Coronary and Peripheral Arteries*, Trends Cardiovasc. Med., vol. 3, No. 5, pp. 163-170 (1993).

Wong et al., *An Update on Coronary Stents*, Cardio, 8 pages (Feb. 1992).

World Precision Instruments, Inc., http://www.wpiinc.com/WPI_Web/Pumps/pneumatic_Fig.gif, printed Sep. 30, 2002, 1 page.

World Precision Instruments, Inc., *Nanoliter Injector*, http://www.wpiinc.com/WPI_Web/Microinjection/Nanoliter_Injector.html, printed Jun. 10, 2005, 3 pages.

World Precision Instruments, Inc., *Nanoliter Injector*, http://www.wpi-europe.com/products/microinjection/nanoliter.htm printed Jun. 10, 2005, 2 pages.

World Precision Instruments, Inc., *Pneumatic PicoPumps*, http://www.wpi_europe.com/products/microinjection/picopumps.htm, printed Jun. 10, 2005, 4 pages.

World Precision Instruments, Inc., *Pneumatic PicoPumps*, http://www.wpiinc.com/WPI_Web/Microinjection/Pneumatic_PicoPumps.html, printed Jun. 10, 2005, 4 pages.

Yau et al., *Modern Size-Exclusion Liquid Chromatography*, Wiley-Interscience Publication, 9 pages (1979).

Yokoyama et al., *Characterization of physical entrapment and chemical conjugation of adriamycin in polymeric micelles and their design for in vivo delivery to a solid tumor*, Journal of Controlled Release, vol. 50, pp. 79-92 (1998).

Yuen et al., *Tissue response to potential neuroprosthetic materials implanted subdurally*, Biomaterials, vol. 8, pp. 57-62 (Mar. 1987).

Zhmud et al., *Dynamics of Capillary Rise*, Journal of Colloid and Interface Science, vol. 228, pp. 263-269 (2000).

Zimarino et al., *Analysis of Stent Edge Restenosis with Different Forms of Brachytherapy*, The American Journal of Cardiology, vol. 89, pp. 322-325 (Feb. 1, 2002).

\* cited by examiner

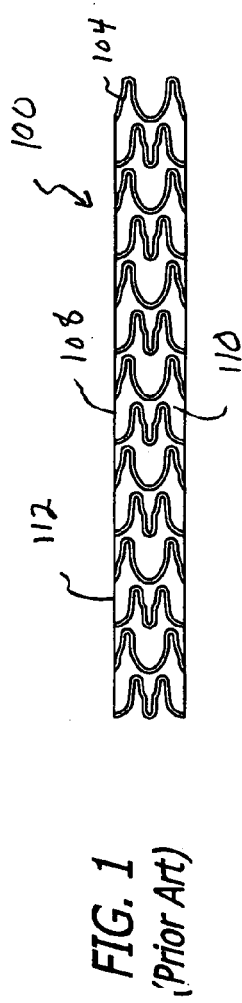
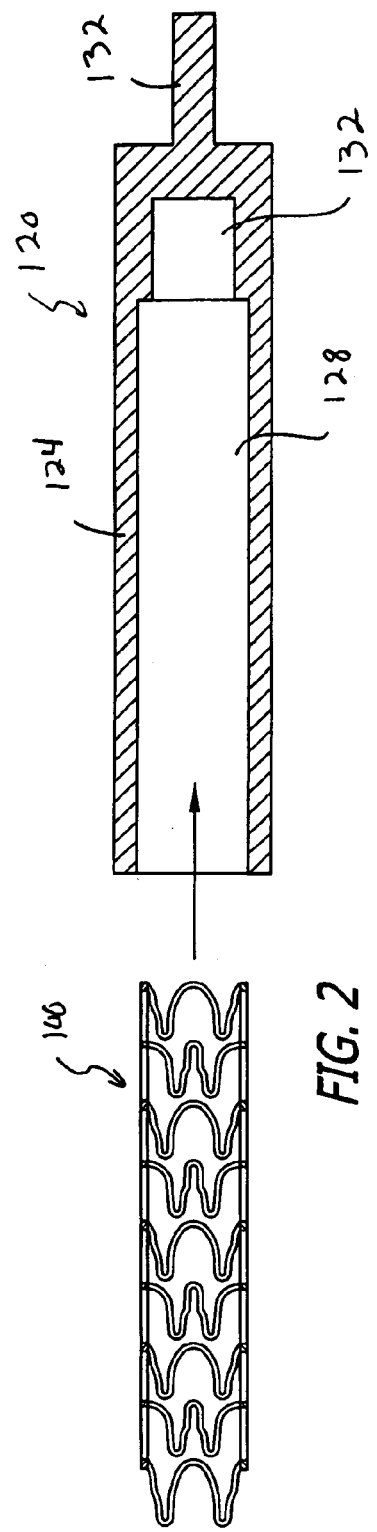
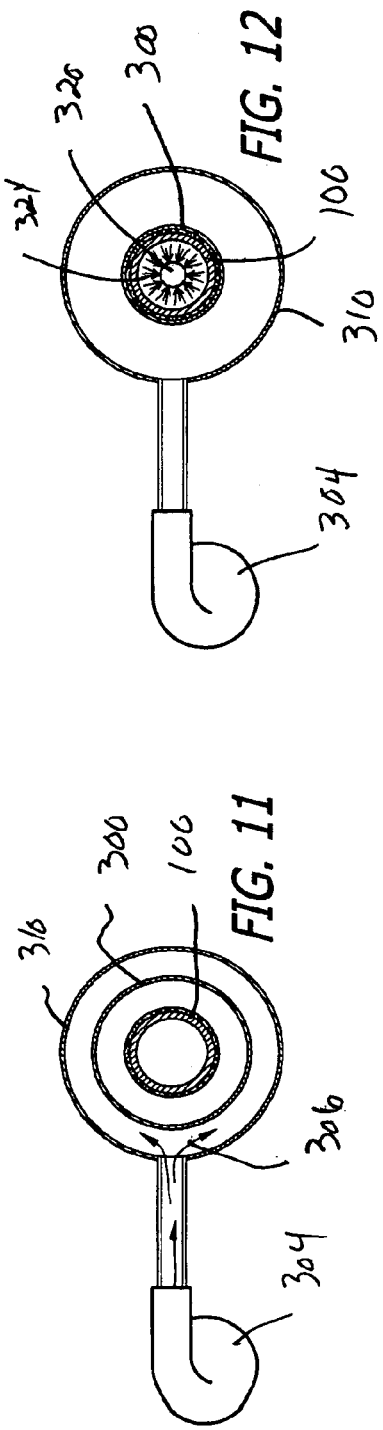
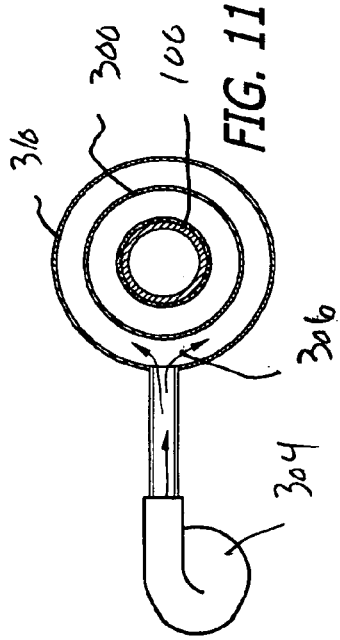
FIG. 1 (Prior Art)
FIG. 2
FIG. 11
FIG. 12

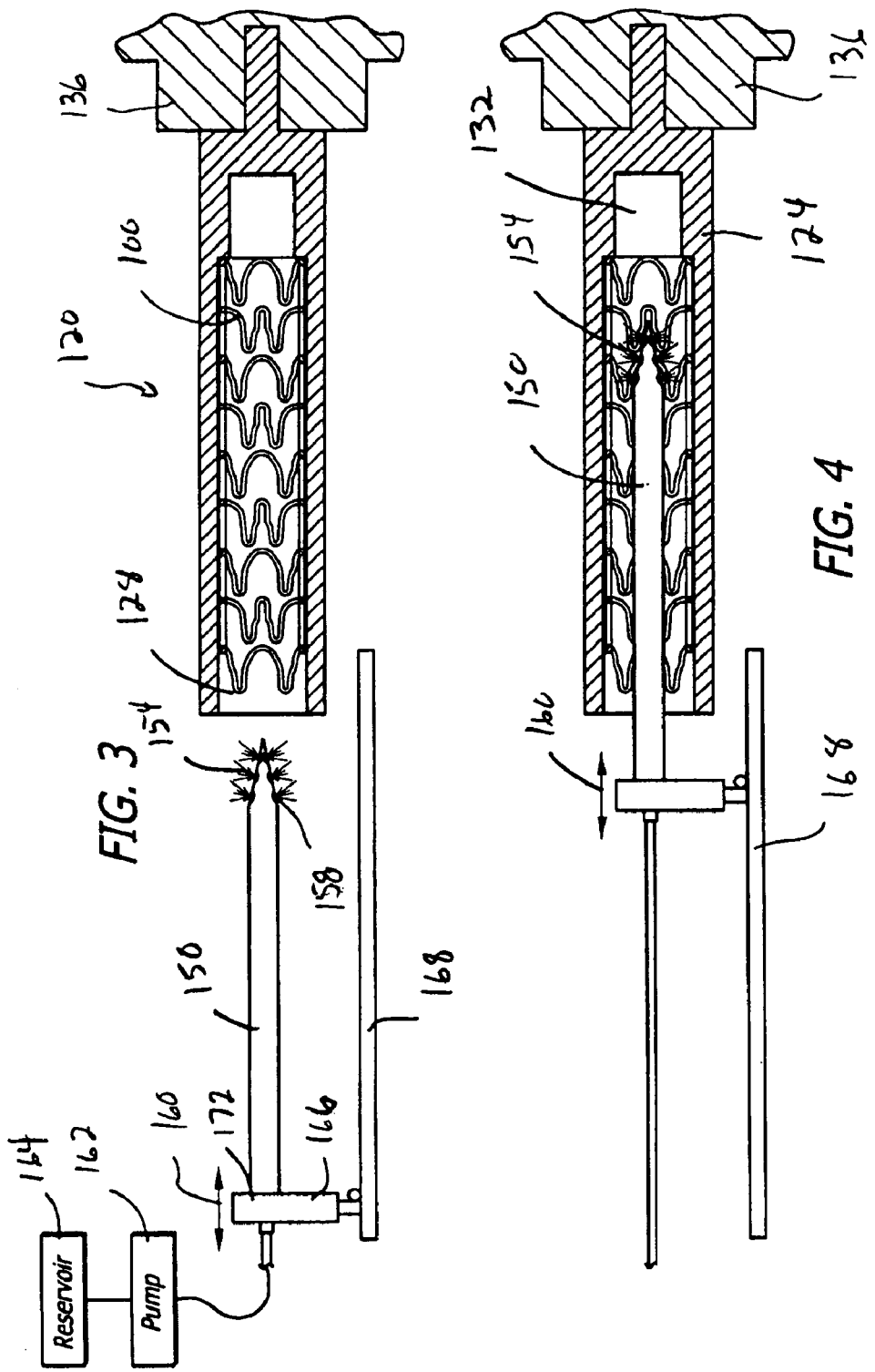

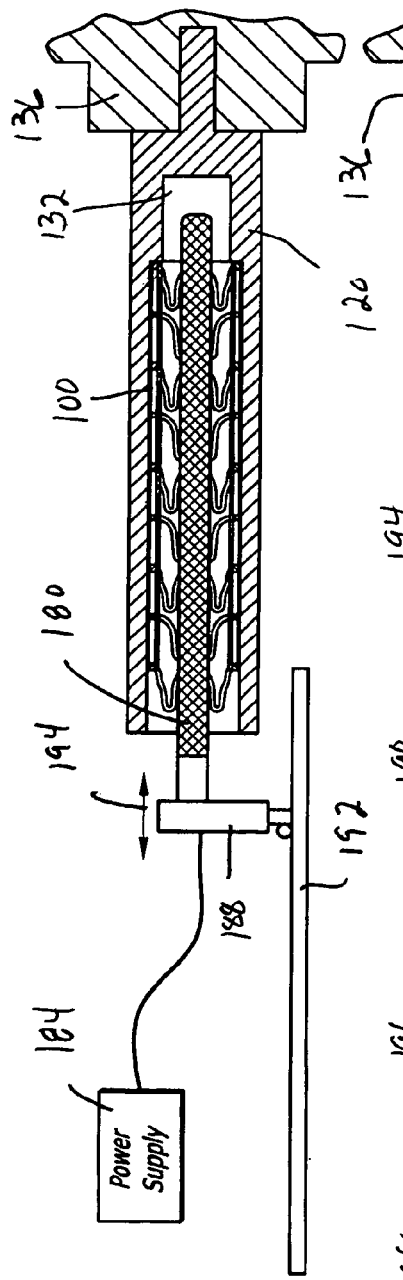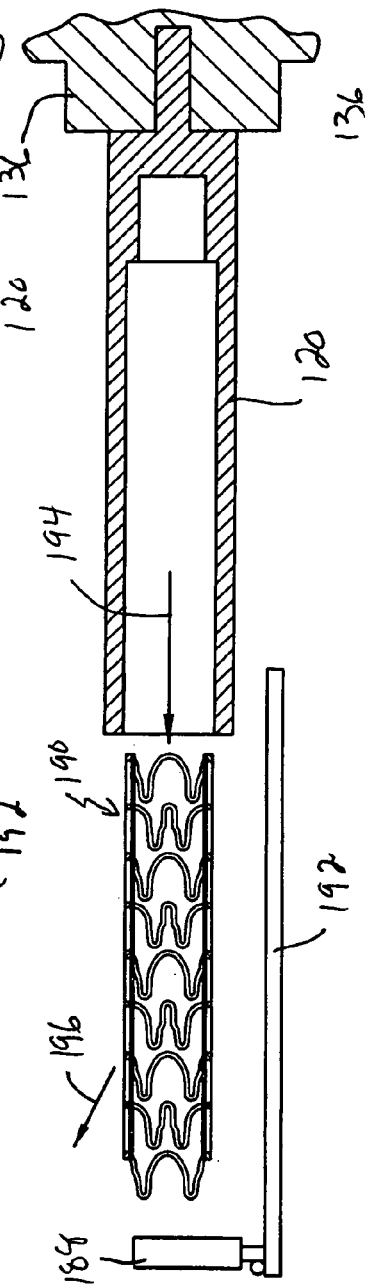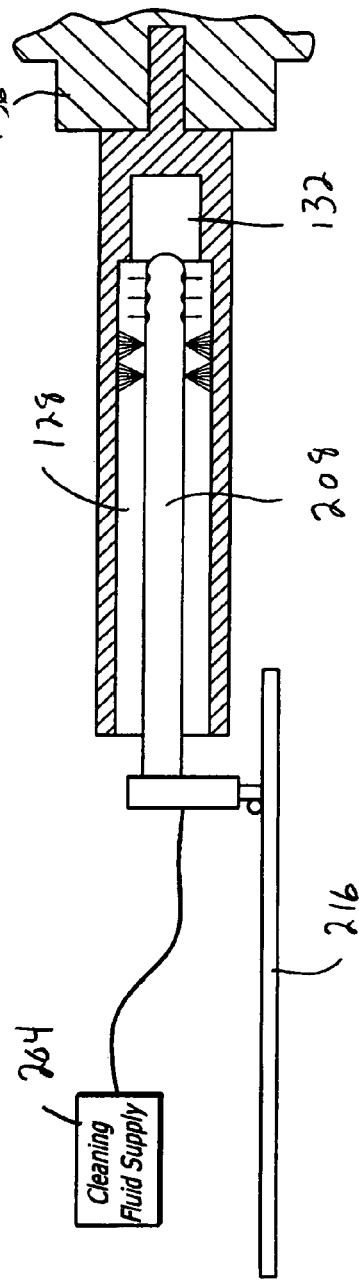

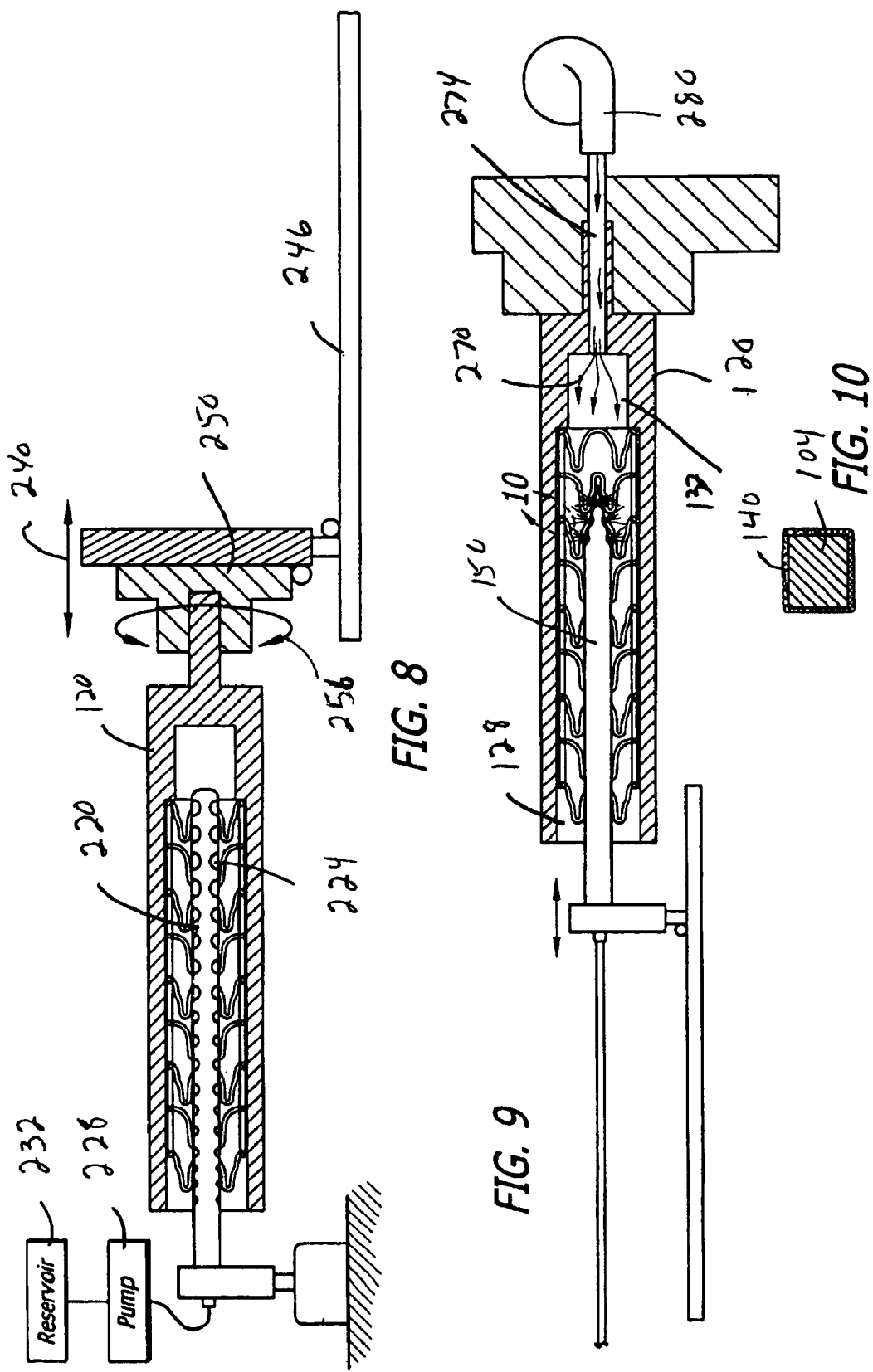

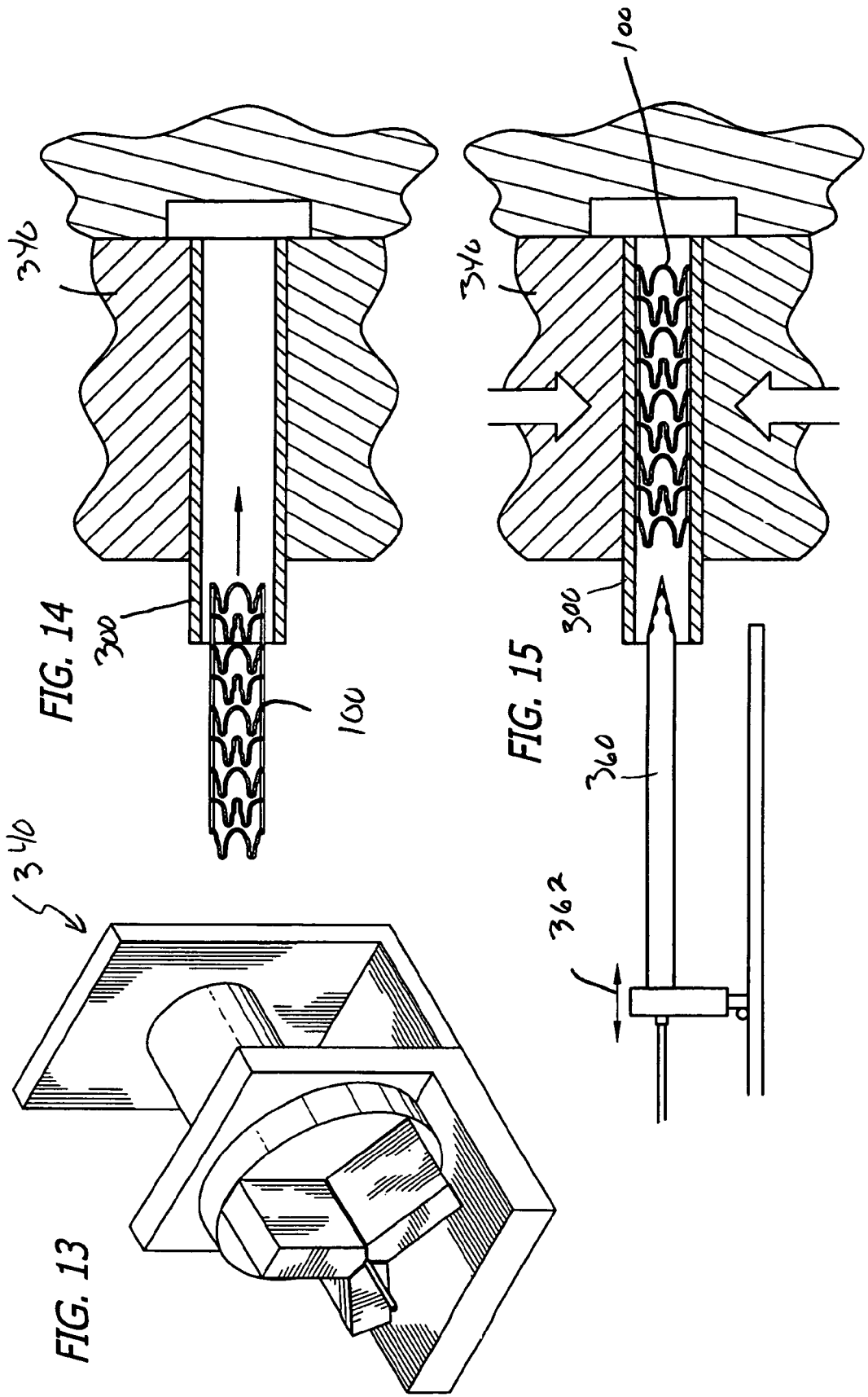

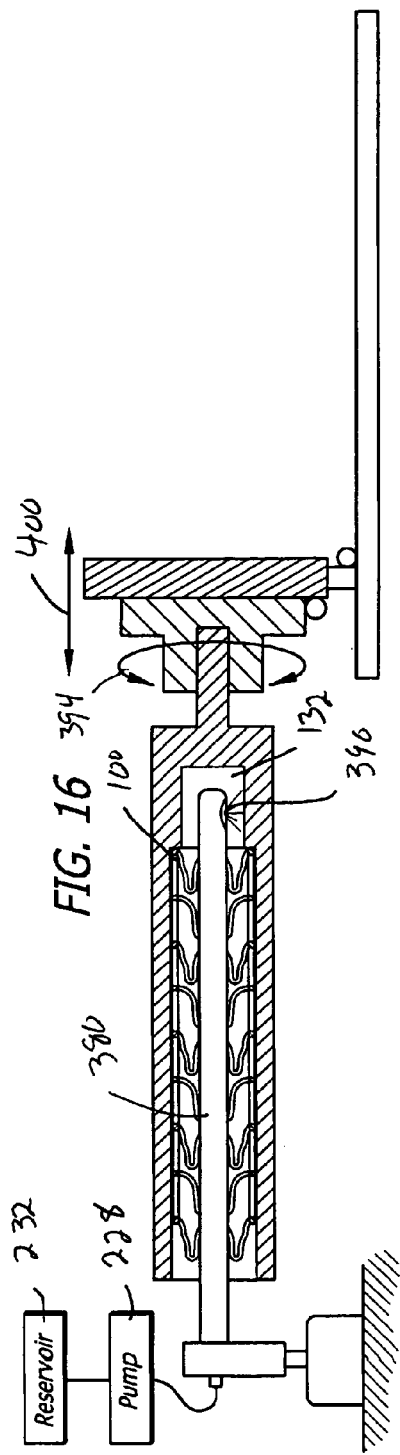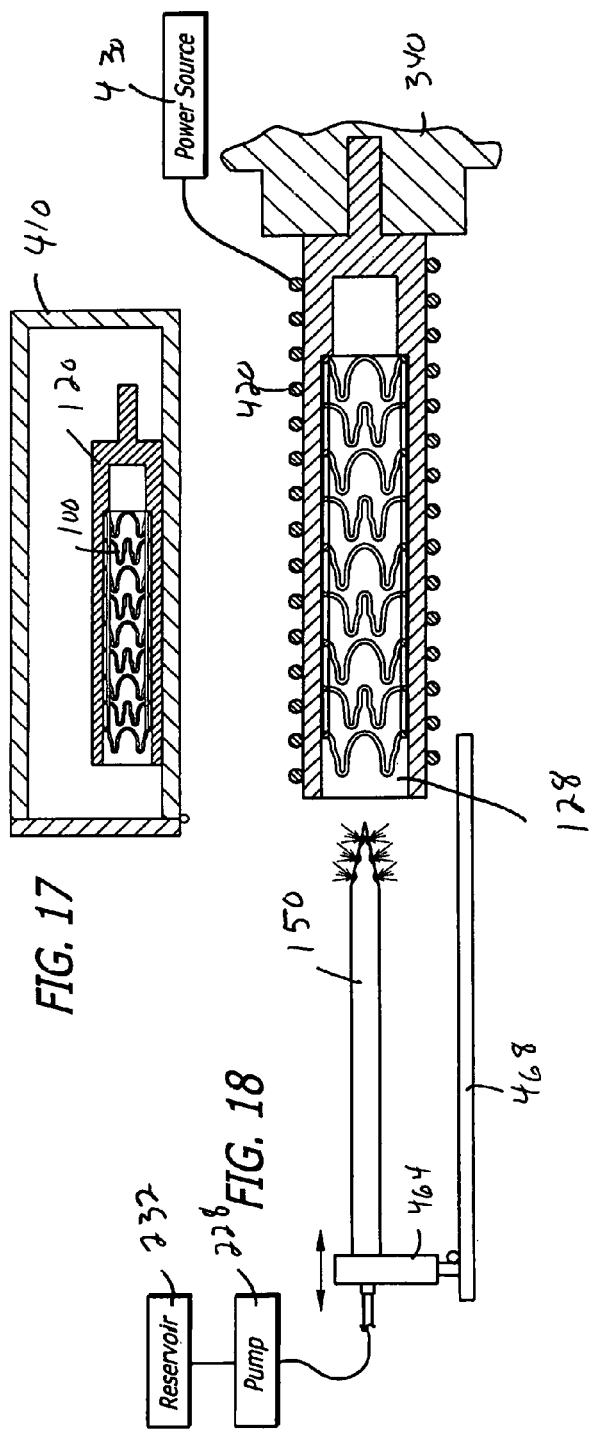

SELECTIVELY COATING LUMINAL SURFACES OF STENTS

BACKGROUND OF THE INVENTION

Blood vessel occlusions are commonly treated by mechanically enhancing blood flow in the affected vessels, such as by employing a stent. Stents act as scaffoldings, functioning to physically hold open and, if desired, to expand the wall of affected vessels. Typically stents are capable of being compressed, so that they can be inserted through small lumens via catheters, and then expanded to larger diameters once they are at the desired location. Examples of stents disclosed in the patent literature include U.S. Pat. No. 4,733,665 (Palmaz), U.S. Pat. No. 4,800,882 (Gianturco), U.S. Pat. No. 4,886,062 (Wiktor), U.S. Pat. No. 5,061,275 (Wallstein), and U.S. Pat. No. 6,605,110 (Harrison), and U.S. 2003/0139800 (Campbell).

FIG. 1 illustrates a conventional stent 100 formed from a plurality of struts 104. The struts 104 are radially expandable and interconnected by connecting elements or links 108 that are disposed between adjacent struts 104, leaving lateral openings or gaps 110 between adjacent struts 104. The struts 104 and the connecting elements 108 define a tubular stent body 112 having an outer, tissue-contacting abluminal surface and an inner, blood flow contacting luminal surface.

Stents are used not only for mechanical intervention but also as vehicles for providing biological therapy. Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered than with systemic dosages that often produce adverse or even toxic side effects for the patient.

One method of medicating a stent uses a polymeric carrier coated onto the surface of the stent. A composition including a solvent, a polymer dissolved in the solvent, and a therapeutic substance dispersed in the blend is applied to the stent by immersing the stent in the composition or by spraying the composition onto the stent. The solvent is allowed to evaporate, leaving on the stent strut surfaces a coating of the polymer and the therapeutic substance impregnated in the polymer. Other known drug deposition methods include roll-coating, electrostatic spraying, and vapor deposition.

SUMMARY OF THE INVENTION

A shortcoming of the above-described methods of medicating stents is that both the inner surface and an outer surface of the stent are coated with the same therapeutic substance. Accordingly, the therapeutic substance will be dispensed locally by being absorbed by the vessel wall from the outer surface of the stent and will be dispensed downstream as blood carries the therapeutic substance from the inner surface of the stent. In some circumstances, there may be a need for coating the outer surface of the stent with a first type of a drug and the inner surface with a second type of a drug. For example, the stent's outer surface could be coated with an anti-inflamatory drug or anti-restenosis drug to treat inflammation or hyper-migration and proliferation of vascular smooth muscle cells, respectively. The stent's inner wall can be coated with an anti-coagulant (or platelet inhibitors or pro-healing agents pursuant to this invention) to reduce platelet aggregation, clotting and thrombus formation.

Thus, directed to remedying problems in the prior art, the present invention provides according to one embodiment thereof, a method which includes masking an abluminal surface of a stent, and coating luminal surfaces of the masked stent with a coating substance.

According to another embodiment of the invention, a coating method is provided which includes compressing a sleeve onto an abluminal surface of a stent to mask the abluminal surface, and coating a luminal surface of the masked stent with a coating substance. The substance can be a polymer-solvent-drug formulation. It can be a platelet inhibitor, an anti-coagulant and/or a pro-healing substance. The pro-healing substance can be a polymer or anti-body coating which facilitates the capture of the endothelial progenitor cells circulating in the bloodstream. The substance can also be an anti-proliferative substance and/or an anti-thrombotic agent or a bioactive coating. The substance coated on stent abluminal surfaces can be a polymer and an anti-proliferative drug coating, or can be a bio-absorbable polymer such as polyactide or polyethylene adipate.

According to a further embodiment of the invention, a coating method is provided which includes coating an abluminal surface of a stent or the entire stent with a first coating substance, and selectively coating a luminal surface of the stent with a second coating substance.

According to another embodiment of the invention, a coating method is provided which includes inserting a heating mechanism into a stent having a luminal coating and thereby curing the luminal coating on the stent.

According to a further embodiment of the invention, a coating method is provided which includes inserting a spray nozzle inside of a stent, and spraying out the spray nozzle a substance on a luminal surface of the stent. This method can include moving rotationally and/or translationally at least one of the spray nozzle and the stent relative to the other during the spraying. After the spraying, the coating can be cured/baked on the luminal surface.

According to a still further embodiment of the invention, a coating method is provided which includes inserting a stent into a chamber of a mandrel, and coating a luminal surface of the inserted stent with a coating substance. The coating can include positioning a spray nozzle into the inserted stent and spraying the coating substance out of the spray nozzle. The mandrel can include a pocket at an end of the chamber, and the positioning can include positioning a tip of the spray nozzle in the pocket. The method can further include after the spraying, inserting a heater mechanism into the inserted stent with a tip of the heater mechanism in the pocket and curing/baking the coating substance onto the luminal surface, or injecting hot gas into the stent to thereby curing/baking the coating substance onto the luminal surface.

According to another embodiment of the invention, a stent construction is provided which includes a stent and a first substance selectively coated on a luminal surface of the stent, and a different second substance coated on abluminal surfaces of the stent.

According to a further embodiment of the invention, a stent coating assembly is provided which includes a compressible sleeve, and compressing means for compressing the sleeve onto abluminal surfaces of a stent positioned therein to thereby mask the abluminal surfaces. The compressing means can be mechanical compressing means or pneumatic compressing means.

According to a still further embodiment of the invention, a stent coating system is provided which includes holding means for holding a stent, and coating means for selectively coating luminal surfaces of the stent, which is held by the holding means, with a coating substance.

According to another embodiment of the invention, a coating method is provided which includes curing/baking the luminal surface coating of a stent. The curing/baking can include positioning the mandrel and stent in an oven, heating the mandrel with a heating mechanism positioned in the stent, directing hot gas into the interior of the stent through an opening in the mandrel, or applying heat to the mandrel via a heating unit (such as a heater coil) on and encircling the mandrel.

According to another embodiment of the invention, a stent coating assembly is provided which includes a mandrel, wherein the mandrel includes chamber means for receiving therein a stent and for masking abluminal surfaces of the received stent such that luminal surfaces of the received stent can be selectively coated with a coating substance.

Other objects and advantages of the present invention will become more apparent to those persons having ordinary skill in the art to which the present invention pertains from the foregoing description taken in conjunction with the accompanying drawings.

BRIEF DESCRIPTION OF THE DRAWINGS

FIG. 1 is a side view of an exemplary stent as is known in the art.

FIG. 2 is a side view showing the stent of FIG. 1 being inserted into a mandrel of one embodiment of the present invention.

FIG. 3 is a side view similar to FIG. 2 with the stent in the mandrel, the mandrel secured in place, and a spray nozzle of the invention ready for insertion into the stent.

FIG. 4 is a view similar to FIG. 3 showing the nozzle in the stent and spray coating the luminal surfaces thereof.

FIG. 5 is a side view showing a heater bar of the invention in the stent after the spray coating of FIG. 4.

FIG. 6 is a view similar to FIG. 5, but after the drying step and showing the luminal surface coated stent being removed from the mandrel.

FIG. 7 is a side view showing the interior surface of the mandrel being cleaned after the luminal surface coated stent has been removed therefrom.

FIG. 8 shows an alternative to the spray coating embodiment of FIG. 4 wherein the nozzle is fixed and the stent is rotated and moved laterally relative thereto.

FIG. 9 is an alternative to the curing/drying embodiment of FIG. 5 wherein instead of a radiating heater bar, the curing/drying is accomplished by injecting hot gas into the opposite end of the mandrel, after the spraying operation.

FIG. 10 is an enlarged view of a portion of the stent taken on circle 10 of FIG. 9 and showing the different abluminal and luminal surface coatings on the stent.

FIG. 11 shows an end view of an alternative mandrel arrangement where instead of a rigid mandrel sleeve as shown in FIG. 2, the "mandrel" is a compressible sleeve mask which is compressed with blown gas (pneumatically) onto the outside surface of the stent.

FIG. 12 shows the sleeve of FIG. 11 in position and the interior of the stent being spray coated.

FIG. 13 is a perspective view of a mechanical compressing mandrel or sleeve assembly, as an alternative to the pneumatic arrangement of FIG. 11, of the invention.

FIG. 14 is an enlarged side sectional view of a portion of the assembly of FIG. 13, showing a stent being inserted into position inside of the compressible sleeve of the assembly of FIG. 13.

FIG. 15 is a view similar to FIG. 14 showing the sleeve being mechanically compressed onto the sleeve, and a spray nozzle being inserted therein to spray coat the luminal surfaces of the stent whose abluminal surfaces have been masked by the compressed sleeve.

FIG. 16 is a view similar to FIG. 8, but showing an alternative spray nozzle construction and with the nozzle fully inserted into the mandrel.

FIG. 17 is a side view showing an alternative drying embodiment wherein the mandrel holding the stent is positioned in a drying oven after the luminal surfaces of the stent have been spray coated.

FIG. 18 is a side view showing an alternative to the drying embodiment of FIG. 5 wherein instead of a heater bar being inserted into the stent, a heater (coil) sleeve positioned around the (tubular) mandrel is energized to heat the mandrel and the coated stent therein.

DETAILED DESCRIPTION OF PREFERRED EMBODIMENTS OF THE INVENTION

The present invention, as discussed in detail below with reference to the drawings, includes methods and apparatuses for selectively coating inner surfaces of stents and other implantable medical devices. Pursuant to a basic aspect of the invention, an outer diameter masking mandrel or a compressible sleeve is positioned about the stent. An inside-out coating process directly coats the inside or luminal surfaces of the stent. The coating is then cured onto the luminal surfaces.

Referring to FIG. 2, a mandrel of an embodiment of the present invention is shown generally at 120. The mandrel 120 has a fixed diameter sleeve 124 defining a rigid cylindrical chamber 128 dimensioned to receive a stent 100 therein. The chamber 128 can have a length equal to or greater than the length of a stent positioned therein. For example, the length can be approximately between ten mm and one hundred and fifty mm and a diameter of approximately between 1.14 mm and 11.00 mm. The mandrel 120 can be constructed of stainless steel, ceramic, glass, or other corrosion-resistant metal. A pocket 132 can be provided at the end of the chamber 128 for reasons which will become more apparent with respect to the descriptions of FIGS. 5 and 8 to follow. The pocket 132 has an opening smaller in diameter than that of the chamber 128. This smaller diameter provides for a rim or shoulder, as best illustrated in the figures, that stops the stent 100 from further penetrating into the chamber 128 or the pocket 132. A "nipple" 132 is provided at the end of the sleeve for fitting into a coating processor or other holding device 136, as shown in FIGS. 3 and 4.

The mandrel 120 is attached to the holding device 136, and the stent 100 is inserted into the mandrel chamber 128. Alternatively, the stent 100 can be inserted into the chamber 128 and then the mandrel 120 fixed into the holder 136. A further alternative is to have the mandrel 120 essentially permanently affixed to a holder. However, it may be advantageous to be able to remove it from the holder for cleaning purposes or for replacement, or for stent curing purposes, as discussed later.

The stent 100 when inserted into the mandrel chamber 128 can already have an abluminal or outer diameter coating 140 and/or can be completely coated. It can be a primered stent, that is, a stent coated with a primer adhesion layer. In other words, the stent 100 may be "drug" or "top coated," but need not be. Alternatively, the inner diameter can be coated first, as by methods disclosed herein, and then the outer diameter coated. (Examples of stent coating methods and coatings are disclosed in U.S. Pat. No. 6,673,154 (Pacetti et al.), U.S. 2003/003221 (Zhong et al.), U.S. 2003/0088307 (Shulze et al.), U.S. 2005/0186248 (Hassainy et al.), U.S. 2004/0071861 (Mandrusov et al.), U.S. Pat. No. 6,673,385 (Ding et al.), U.S. 2005/0192662 (Ward), U.S. 2005/0107531 (Claude) and U.S. 2005/010623 (Roorda et al.).) The outer diameter can be selectively coated, for example, by using an inner diameter masking mandrel, such as that disclosed in U.S. 2005/0069630 (Fox et al.)

Referring now to FIG. 3, with the stent 100 in position in the mandrel chamber 128 and the mandrel securely held in, preferably, a horizontal orientation, a spray nozzle 150 is inserted into the stent 100 and a coating 154 is sprayed onto the luminal surfaces of the stent 100. The spray nozzle 150 of FIG. 3 can have openings 158 three hundred and sixty degrees around the tip. The spray nozzle 150, inserted into the stent 100 as shown by the arrow 160 in FIG. 3, can be moved or oscillated back and forth laterally within the stent 100 to coat the stent surface as desired. A pump 162 to pump the coating substance from reservoir 164 can be used as well. The nozzle 150 can be moved by a powered trolley 166 running along a track 168. It should be noted that with any applicable embodiment disclosed herein, any one or a combination of the following movement can be used: rotation of the nozzle, linear movement of the nozzle, rotation of the stent, and linear movement of the stent.

The spray nozzle 150 can be a "pin" spray, smaller than the inner diameter of the stent 100, and made of stainless steel or other solvent-compatible material. This nozzle can have a hollow center providing the fluid path for the coating material. The tip of the nozzle 150 can be machined to permit a circular spray pattern, for example. The "pin sprayer" can be fitted inside a block 172 attached to the sprayer and attached at its backside to the fluid reservoir 164, similar to known syringe pump mechanisms.

The coating substance 154 can include a platelet inhibitor (such as Dipyridamole, Ticlopidine, Abciximab or Clopidigrel), an anti-coagulant (such as heparin, low molecular weight heparin or warfarin) and/or an agent used to capture endothelial progenitor cells (such as polysaccharide, collagen or fullerenes). See, George et al., "Number and Adhesive Properties of Circulating Endothelial Progenitor Cells in Patients with In-Stent Restenosis", Arteriosclerosis, Thrombosis, and Vascular Biology, 2003; 23; e57. See also Aoki et al., "Endothelial Progenitor Cell Capture by Stents Coated With Antibody Against (D34: the Healing-FIM (Healthy Endothelial Accelerated Lining Inhibits Neointimal Growth-First In Man) Registry," J. Am. Coll. Cardiol. 2005 May 17; 45(10): 1574-9. Additional inner diameter coatings include therapies such as anti-thrombotic agents, for reduction of fibrinogen and other thrombotic factors, and vasodilators, for increased diameter post-stent implantation. The coating applied to the luminal surface of the stent 100 can have a thickness of two to ten microns or more narrowly, four to six microns. The coating substance can include a polymer for include a drug free from any polymers. In some embodiments, the coating substance can be a bio-adhesive for improving stent retention of a catheter balloon.

After the coating step, the coating can be cured or baked onto the inner diameter of the stent 100. One method of doing this pursuant to the present invention is to insert a cylindrical electrical resistance heater bar 180 into the stent 100. This is shown in FIG. 5, where the heater bar 180 is powered by a power supply 184 and a powered trolley 188, traveling on a track 192, moves the bar controllably back and forth as indicated by arrow 194 in the stent 100 to dry the coating. The curing can be for between one and three minutes and at a temperature of approximately forty-five degrees Centigrade.

The heating coil or bar 180 can be adjusted to a specific temperature to deliver a prescribed amount of heat to cure the coating before the stent 100 is removed from the mandrel. In other words, a cylindrical heat nozzle element with programmable temperature capabilities can be used to provide the heat needed to cure the inner diameter coating. There can be a drying period at ambient between the coating steps. After the luminal coating and before the final curing, the coating can be dried at ambient temperatures for approximately at least ten to fifteen seconds. In some embodiments, the length of the bar 180 can be the same or longer than the length of the stent 100 so as to provide for an even distribution of heat across the length of the stent 100. Referring to FIG. 5, the tip of the heater bar 180 when fully inserted into the stent can extend into the pocket 132 to thereby ensure that the substance on the distal end of the stent is fully and evenly cured.

Additional coating and curing steps may be conducted on the stent 100 as desired to coat the stent with the same substance or to coat it with different substances at different steps, as would be within the skill of those in this art from this disclosure. The entire stent surface can be first coated with a polymer and an anti-proliferative drug such as everolimus. Afterwards, an anti-coagulant or anti-thrombotic polymer coating can be applied to the stent inner diameter, and optionally sidewall surfaces, for example, by using the above-discussed mandrel or the below-discussed compressible sleeve. These successive steps may need inter-pass drying (or drying between coating steps). There may or may not be an oven bake or other curing process between application of the two different formulations, and this can depend on desired release kinetics and solvents used. In other words, a two-phase coating process can be used, namely: (1) with an anti-proliferative, and (2) with an anti-thrombotic agent or a natural biocoating (one that adheres endothelial progenitor cells for strut re-endothelialization). The order of coating can be either (1) then (2), or (2) then (1). It is also within the scope of the invention to blanket the stent 100 with a polymer "topcoat" to slow, retard or encapsulate the dual-therapies.

Most coatings need a final (oven) baking/curing process to drive off the remaining solvent. Temperature and time conditions are based on the solvent that is to be removed. The goal is to reduce residual solvent to a safe, non-toxic, perhaps non-detectable level, which reduces the risk of an adverse reaction by the body to the solvent. Ambient drying can be used, but it depends on the solvent. More particularly, existing formulations require oven baking or other curing to remove excess solvents. Any solvent which evaporates at room temperature might be too volatile to effectively spray coat as the solvent might evaporate before the spray droplets contact the stent surface. In addition, some initial residual solvent is desirable to allow the coating to create a uniform surface on the stent before drying.

The final drug baking can be at fifty degrees Centigrade for sixty to seventy-five minutes. This time/temperature would vary based on any adverse reaction or damage to the drug, the type of solvent being forcibly evaporated from the stent, and the desired release kinetics of the drug. Drying or solvent removal from the coating may have a significant impact on drug release kinetics upon implantation of the stent in the body of the patient.

After the coating and curing have been completed, the selectively coated stent 190 is removed from the mandrel 120 as shown by the arrows 194, 196 in FIG. 6, for any further manufacturing steps as may be needed.

The inside of the mandrel chamber 128 can then be cleaned. Referring to FIG. 7, this can be by using a cleaning fluid 200 from a supply 204 and sprayed out of a spray nozzle 208, which is mechanically driven back and forth on a track 216, to clean the inner circumference of the chamber 128. The chamber 128 can then be air dried and/or dried with a drying implement, as needed. This cleaning step may be done after each stent 100 is coated or as otherwise needed.

An alternative method of coating the luminal surfaces of the stent 100 is to have the spray nozzle 220 fixed and to move the mandrel 120 and thereby the stent 100 relative to the spray nozzle 220, as illustrated in FIG. 8. The spray nozzle 220 can have nozzle openings 224 along its entire length. The ones at the distal end can be slightly larger than ones at the proximal end as shown (in an exaggerated manner) in FIG. 8 to take into account spray fluid pressure drops. The coating material can be pumped by a pump 228 from a reservoir 232 and out through the openings 224 in the nozzle 220, as the mandrel 120 and thereby the stent 100 therein is moved translationally relative thereto as shown by arrow 240. This movement can be by a motorized movement along a track 246. If the nozzle openings extend a full three hundred sixty degrees around the nozzle, it may not be necessary to rotate the stent 100 around the nozzle 220. However, if they are not completely around the nozzle or as an alternative process, the stent can be rotated by the motor mechanism 250 as indicated by the circular arrow 256 in FIG. 8. Rotation of the stent 100 may provide for a more uniform application of the coating substance.

While an electrical resistance heater bar 180 for curing the coating material is illustrated in FIG. 5, an alternative is to use heated gas 270 (such as air) as shown in FIG. 9. This can, for example, be a "dry gas" or an inert gas so that curing/baking occur simultaneously. Referring to this drawing figure, the mandrel 120 can have a channel 274 at its end opposite to the stent insert end and communicating with the pocket 132 and thereby the chamber 128. A pump shown schematically at 280 can pump hot gas 270 into the interior of the stent 100 as shown by the arrows in FIG. 9. This can be done as the spray nozzle 150 is being removed as illustrated in FIG. 9 or after the spray nozzle 150 has been removed and ambient drying has occurred for a time. In some embodiment, one skilled in the art may appreciate that application of the gas may be suitable if conducted simultaneously with the coating deposition process. FIG. 10 illustrates an enlarged view of a strut 104 of the stent after a coating operation and showing the coating.

The mandrel 120 provides a fixed, rigid receiving chamber 128 for the stent 100. An alternative is to provide a compressible member and means for compressing the member onto the outside surface of the stent 100. This alternative arrangement does not require the tight exact tolerances of the rigid mandrel and also can compress tightly onto the abluminal surfaces of the struts of the stent and a very slight dimension into the cells or openings between struts. The compressible member can be a compliant sleeve 300 such as shown in end view in FIG. 11. The sleeve 300 can have a wall thickness of 0.005-0.010 inch, and can be made of a low Durometer (40-70 D) Pebax, Tecoflex or similar elastomer. A means for compressing this sleeve 300 is illustrated schematically as a pneumatic means where a pump 304 is provided to pump air 306 or other gas into a chamber 310 around the sleeve 300 and thereby compress the sleeve 300 onto the stent 100. The sleeve 300 is held on the stent 100 with the pneumatic pressure while the spray nozzle is inserted into the held stent 100 and the coating material sprayed thereon. The spray nozzle is shown in FIG. 12 at 320 and the coating material being sprayed is shown at 324 emanating therefrom. The pneumatically compressed sleeve 300 can also hold the stent while the sprayed substance is cured onto the luminal surfaces. This can be by a heater bar inserted therein, such as shown in FIG. 5, or by hot air injected through it similar to the method shown in FIG. 10.

Instead of pneumatically compressing the sleeve 300 onto the outer surface of the stent 100, the sleeve 300 can be mechanically compressed, as can be understood from FIGS. 13-15. Referring to FIG. 13, a mechanical radial-type crimper as shown generally at 340 can be used, and shown in enlarged partial cross section in FIGS. 14 and 15. In FIG. 14 it is shown in a normal or relaxed state with the sleeve 300 held therein and the stent 100 being inserted or positioned into the sleeve 300. FIG. 15 then shows with large arrows the sleeve 300 being compressed (for example by moving jaws of crimper 340 radially by electrical, pneumatic or hydraulic means) onto and around the stent 100 in a masked arrangement.

In this masked arrangement, with the abluminal surfaces of the stent 100 covered with the sleeve 300, the spray nozzle 360 can be inserted into the stent and the luminal surfaces sprayed with the coating material. This can be with a translational movement of the nozzle along the length of the stent (as depicted by arrow 362), and/or the stent 100 can be rotated and/or moved translationally relative to the nozzle as shown for the alternative embodiments for the mandrel arrangement. Additionally, a pocket similar to the mandrel pocket 132 can be provided in the mechanical or pneumatic sleeve compression arrangements.

FIG. 16 illustrates an alternative mandrel arrangement (or compressible sleeve arrangement) where the nozzle 380 does not have openings around its entire circumference, but rather only has openings around a partial part of the circumference such as a single opening 390 on a bottom surface thereof. To spray coat the entire circumference of the inner diameter of the stent 100, the stent 100 can then be rotated about the longitudinal axis of the nozzle 380 as indicated by the circular arrow 394 in FIG. 16. Further, the stent 100 can be moved translationally relative to the length of the nozzle 380, as shown by the arrow 400. FIG. 16 illustrates how the tip of the nozzle 380 can extend into the pocket 132 to thereby ensure that the most distal end portions of the stent 100 are completely coated.

An alternative means of curing the coating onto the inner diameter of the stent 100 is illustrated generally in FIG. 17 where the stent 100 conveniently held still in the mandrel 120 is positioned in a conventional baking oven 410. It is kept therein at the desired temperature and for the time needed for curing.

A further alternative means for curing the coating onto the inner diameter of the stent 100 is to use a heater sleeve. This sleeve is shown in FIG. 18 by a heater coil 420 powered by the power source 430 and wrapped around the outer diameter of the sleeve of the mandrel. When the coil 420 is energized, heat is transmitted through the mandrel into the chamber 128 to thereby cure the coating onto the inner diameter of the stent 100. Also illustrated in FIG. 18 is the spray nozzle 150 after a spraying operation and after having been removed from the stent 100. The pump and reservoir are shown schematically in this figure at 232 and 228, respectively, as is the trolley 464 for moving the stent 100 along the track 468.

Instead of spray coating the luminal surfaces they may be roll coated, dip coated, vapor deposition coated or electrostatic coated, as would be apparent to those skilled in the art from the present disclosure. Examples of electrostatic coating techniques are disclosed in U.S. Pat. No. 5,824,049 (Ragheb et al.), U.S. Pat. No. 6,096,070 (Ragheb et al.) and U.S. Pat. No. 6,669,980 (Hansen).

In summary, existing drug eluting or delivery stent therapies effectively provide localized therapies to the vessel wall where injury occurs upon stent placement. Stents of the present invention are coated with a therapy specific to the luminal surface and thereby effectively deliver local treatments into the bloodstream. Therapies which can be delivered by the inner diameter coatings are platelet inhibitors, anticoagulants and pro-healing substances. Additional inner diameter coating therapies include anti-thrombotic agents and vasodilators.

From the foregoing detailed description, it will be evident that there are a number of changes, adaptations and modifications of the present invention which come within the province of those skilled in the art. The scope of the invention includes any combination of the elements from the different species or embodiments disclosed herein, as well as subassemblies, assemblies, and methods thereof. However, it is intended that all such variations not departing from the spirit of the invention be considered as within the scope thereof.

What is claimed is:

1. A coating method, comprising:
   masking an abluminal side of a stent including positioning the stent within an interior chamber of a sleeve, the sleeve including a proximal end opening and a distal end channel in fluid communication with the chamber;
   coating a luminal side of the masked stent with a coating substance; and
   curing the coating including supplying a gas to the chamber by way of the channel.

2. The method of claim 1 wherein the sleeve has a fixed interior diameter.

3. The method of claim 2 wherein the sleeve comprises a pocket and the chamber in fluid communication with the channel.

4. The method of claim 1 further including disposing a spray nozzle at least partially within a bore of the stent when spraying the coating substance.

5. The method of claim 4 wherein the spraying includes moving the masked stent relative to the spray nozzle.

6. The method of claim 4 wherein the spraying includes moving the spray nozzle relative to the masked stent.

7. The method of claim 1 wherein the coating substance is a polymer-solvent-drug formulation.

8. A coating method, comprising:
   masking an abluminal side of a stent; and
   spray coating a luminal side of the masked stent with a coating substance;
   wherein the masking includes positioning the stent in a chamber of a masking sleeve; and
   wherein the sleeve has a pocket at a distal end of the chamber, and the coating includes positioning a tip of a spray nozzle in the pocket.

9. The method of claim 8,
   further comprising after the spray coating, removing the coated stent from the chamber and cleaning the chamber.

10. A coating method, comprising:
    masking an abluminal side of a stent; and
    coating a luminal side of the masked stent with a coating substance;
    wherein the masking includes positioning the stent within a compressible masking sleeve.

11. The method of claim 10 wherein the masking includes compressing the masking sleeve onto the abluminal side using compressed air.

12. The method of claim 10 wherein the masking includes mechanically compressing the sleeve.

13. The method of claim 10 wherein the masking includes pneumatically compressing the sleeve.

14. The method of claim 10 wherein the masking includes compressing the masking sleeve onto the abluminal side using a crimper.

15. A coating method, comprising:
    masking an abluminal side of a stent;
    coating a luminal side of the masked stent with a coating substance; and
    inserting a heater into the bore of the masked stent and curing the coating substance onto the luminal side;
    wherein the masking includes positioning the stent in a sleeve, the sleeve including a chamber and a pocket at a distal end of the chamber; and
    wherein the curing includes positioning a distal tip of the heater in the pocket.

16. A coating method, comprising:
    masking an abluminal side of a stent; and
    coating a luminal side of the masked stent with a coating substance;
    wherein the stent is a primer adhesion layer coated stent.

17. A coating method, comprising:
    compressing a sleeve onto an abluminal side of a stent to mask the abluminal side; and
    coating a luminal side of the masked stent with a coating substance.

18. The method of claim 17 wherein the coating is by spray coating, roll coating, electrostatic coating or vapor deposition coating.

19. The method of claim 17 wherein the compressing includes mechanical compressing.

20. The method of claim 19 wherein the mechanical compressing uses a radial closure mechanism.

21. The method of claim 17 wherein the compressing includes pneumatic compressing.

22. The method of claim 17 wherein the sleeve is a compliant plastic sleeve.

23. The method of claim 17 wherein the coating includes inserting a nozzle into the masked stent and spray coating the luminal side with the nozzle.

* * * * *